(12) United States Patent
Barzilay

(10) Patent No.: US 10,835,374 B2
(45) Date of Patent: Nov. 17, 2020

(54) INTRAOCULAR LENS AND METHODS AND/OR COMPONENTS ASSOCIATED THEREWITH

(71) Applicant: Gilad Barzilay, Givat Elah (IL)

(72) Inventor: Gilad Barzilay, Givat Elah (IL)

( * ) Notice: Subject to any disclaimer, the term of this patent is extended or adjusted under 35 U.S.C. 154(b) by 105 days.

(21) Appl. No.: 16/093,638

(22) PCT Filed: Apr. 30, 2017

(86) PCT No.: PCT/IB2017/052515
§ 371 (c)(1),
(2) Date: Oct. 14, 2018

(87) PCT Pub. No.: WO2017/191542
PCT Pub. Date: Nov. 9, 2017

(65) Prior Publication Data
US 2019/0125523 A1 May 2, 2019

Related U.S. Application Data

(60) Provisional application No. 62/330,528, filed on May 2, 2016.

(51) Int. Cl.
*A61F 2/16* (2006.01)
*H01L 41/193* (2006.01)
(Continued)

(52) U.S. Cl.
CPC .......... *A61F 2/1635* (2013.01); *H01L 41/098* (2013.01); *H01L 41/193* (2013.01); *H02N 1/04* (2013.01); *H04N 7/18* (2013.01); *A61F 2/1618* (2013.01); *A61F 2002/1681* (2013.01); *A61F 2002/1682* (2015.04); *A61F 2002/16902* (2015.04); *A61F 2002/482* (2013.01); (Continued)

(58) Field of Classification Search
CPC .............. A61F 2/1635; A61F 2002/482; A61F 2250/0003; G02C 7/085; G02B 26/005
See application file for complete search history.

(56) References Cited

U.S. PATENT DOCUMENTS 5,443,506 A 8/1995 Garabet
2008/0188930 A1 8/2008 Mentak et al.
(Continued)

FOREIGN PATENT DOCUMENTS

WO WO-2010004094 A1 * 1/2010 .......... A61F 2/1627
WO 2015/123616 8/2015
WO 2015/138507 9/2015

OTHER PUBLICATIONS

Shian et al., "Tunable lenses using transparent dielectric elastomer actuators," Optics Express, Apr. 2, 2013, vol. 21, No. 7, pp. 8699-8676.

*Primary Examiner* — David H Willse
*Assistant Examiner* — Javier G Blanco
(74) *Attorney, Agent, or Firm* — The Law Office of Joseph L. Felber

(57) ABSTRACT

An intraocular lens (IOL) has a clear optic and a curvature changing mechanism in at least a portion the clear optic. The intraocular lens (IOL) can have anterior and posterior portions spaced apart by a cavity, and an actuator for urging change in curvature in at least one of the portions, with energy provided by an energy harvesting mechanism incorporated into haptics of the IOL.

20 Claims, 22 Drawing Sheets

(51) Int. Cl.
  *H04N 7/18*   (2006.01)
  *H01L 41/09*  (2006.01)
  *H02N 1/04*   (2006.01)
  G02C 7/08    (2006.01)
  G02B 26/00   (2006.01)
  A61F 2/48    (2006.01)
(52) U.S. Cl.
  CPC .... *A61F 2250/0003* (2013.01); *G02B 26/005* (2013.01); *G02C 7/085* (2013.01)

(56) References Cited

U.S. PATENT DOCUMENTS

| | | | | |
|---|---|---|---|---|
| 2010/0208357 A1* | 8/2010 | Batchko | ................ | G02B 5/20 |
| | | | | 359/666 |
| 2011/0149410 A1* | 6/2011 | Blum | .................. | G02B 3/14 |
| | | | | 359/666 |

* cited by examiner

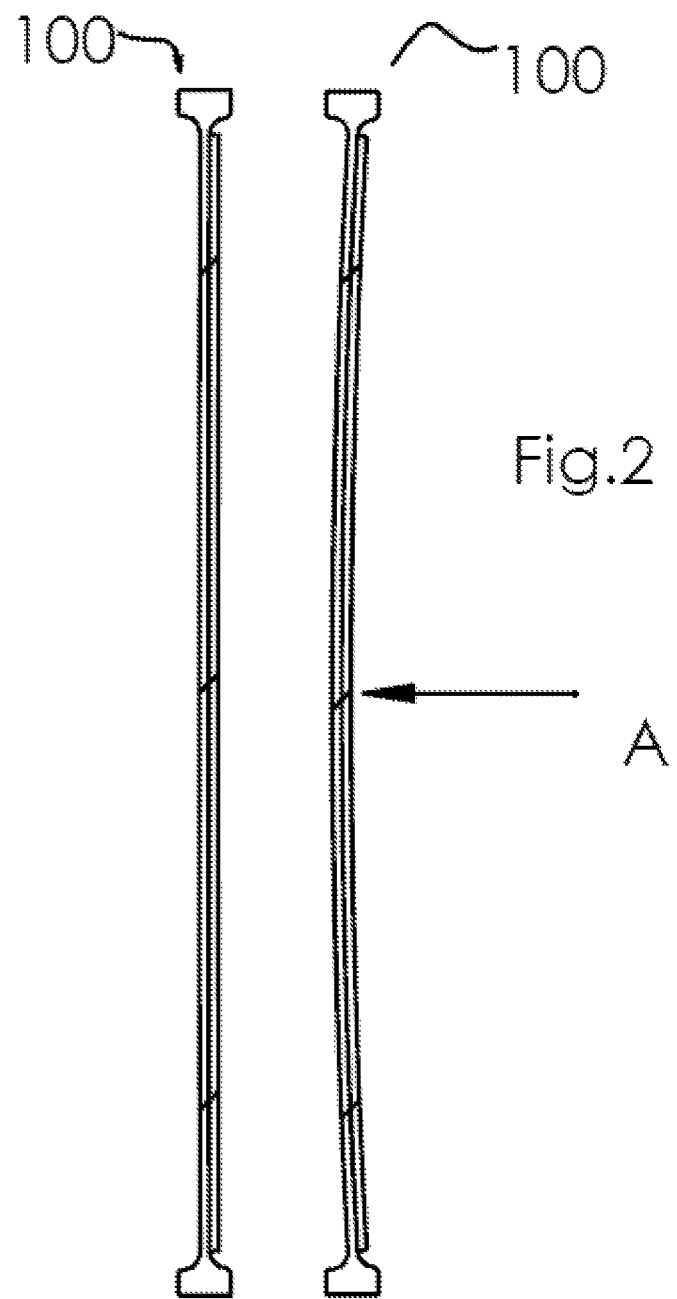

Anterior          Posterior
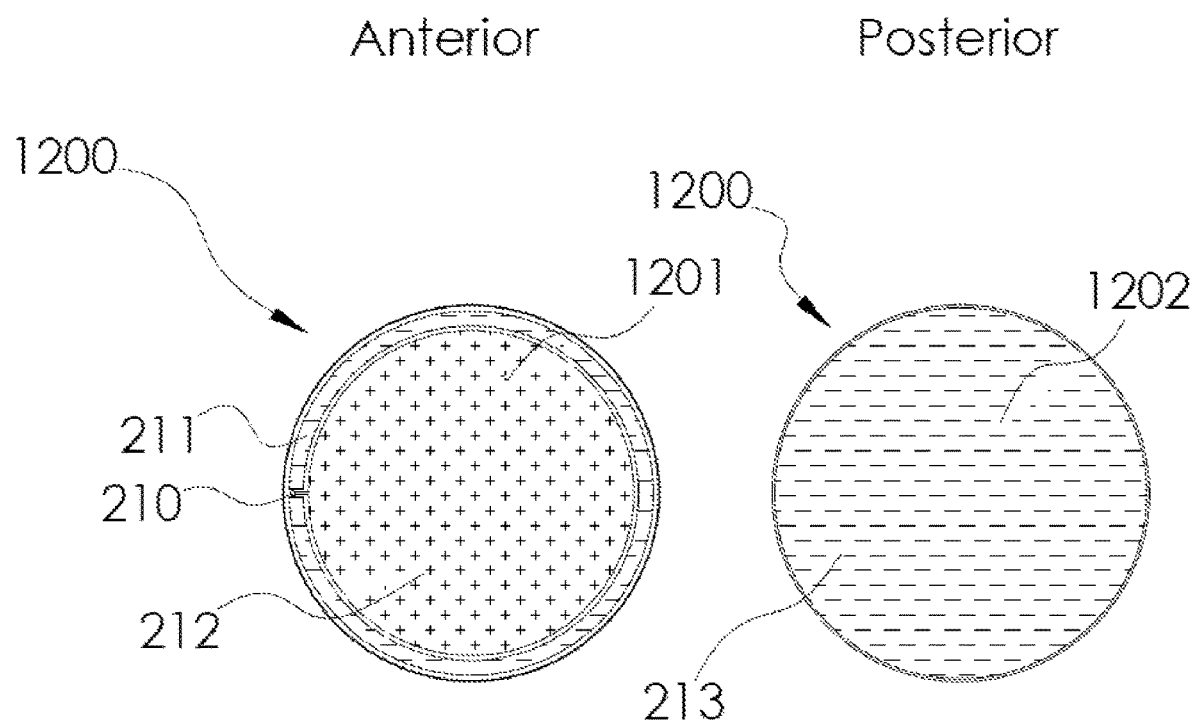
Fig. 2a
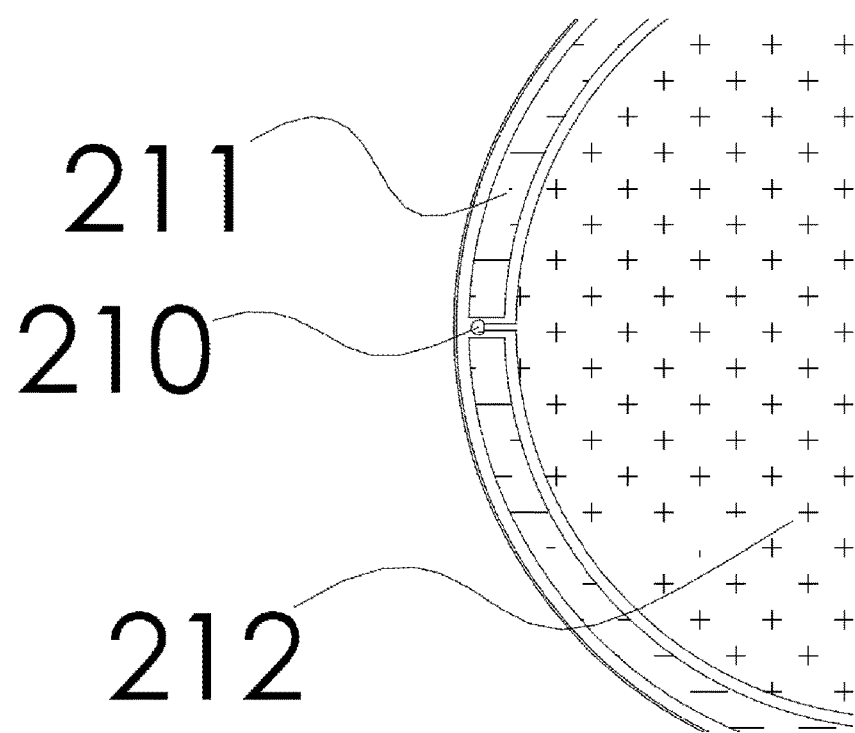

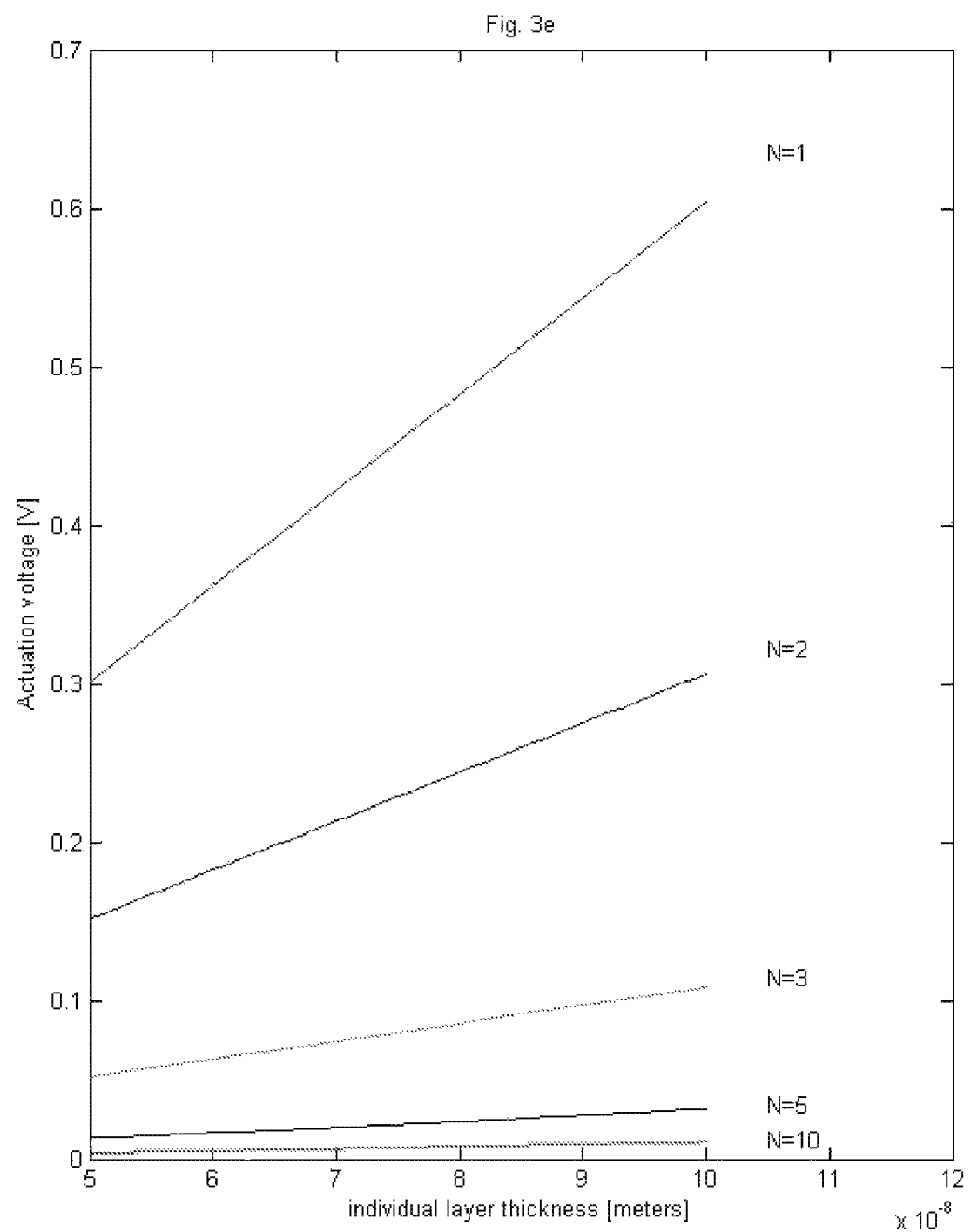

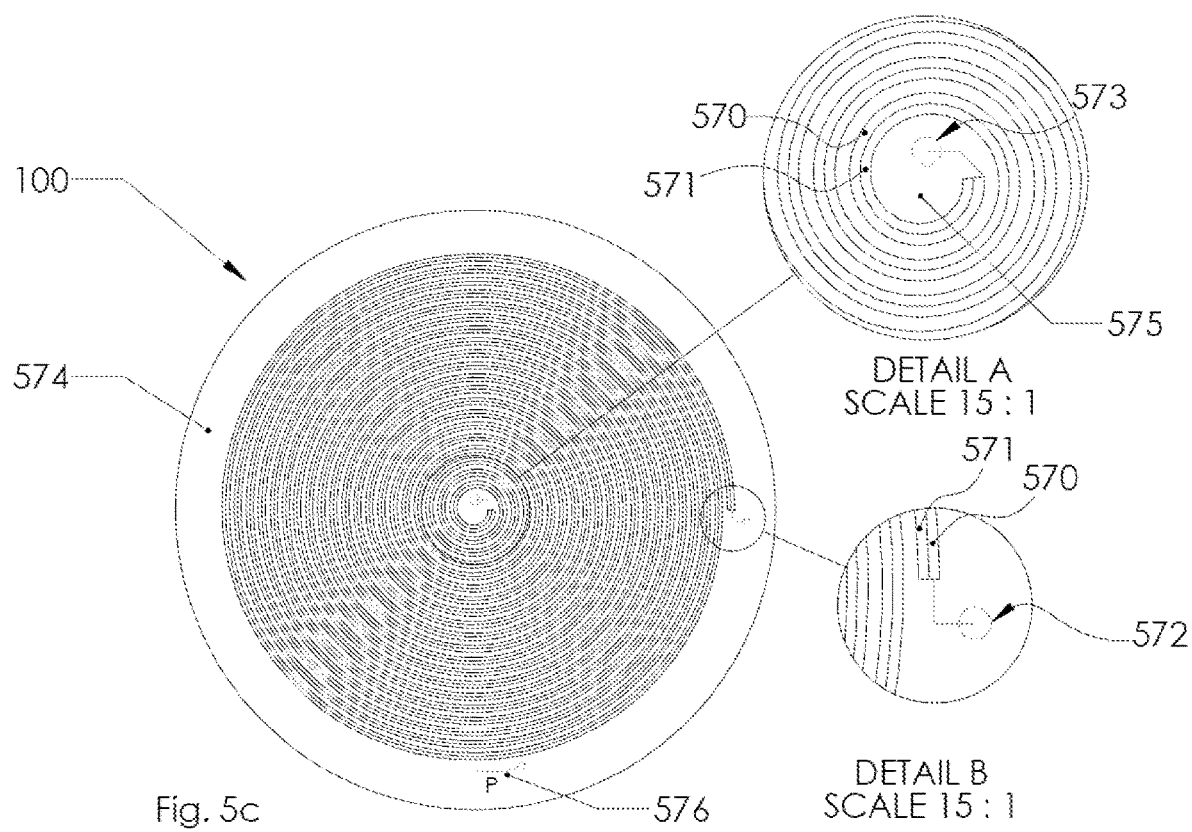

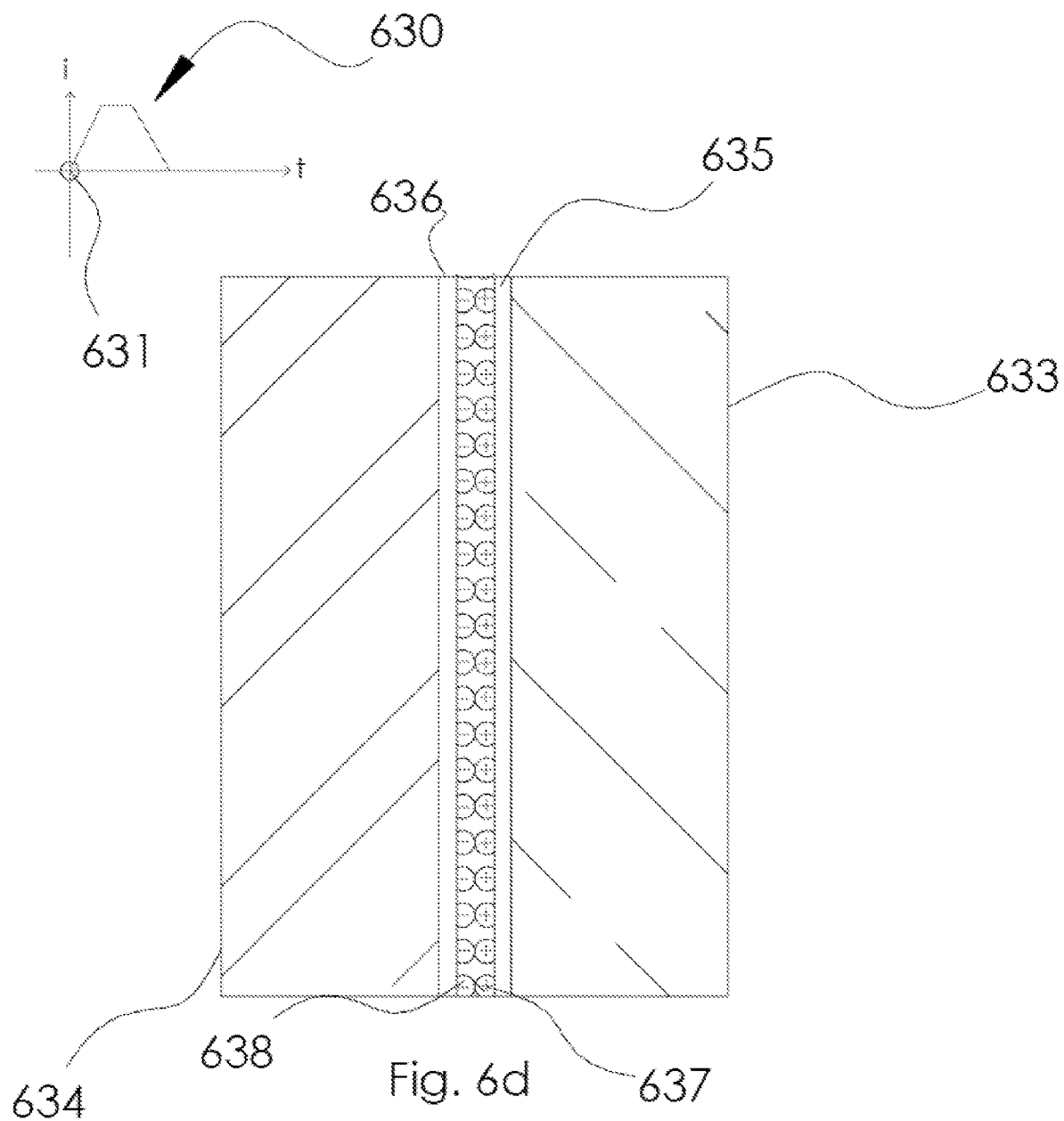

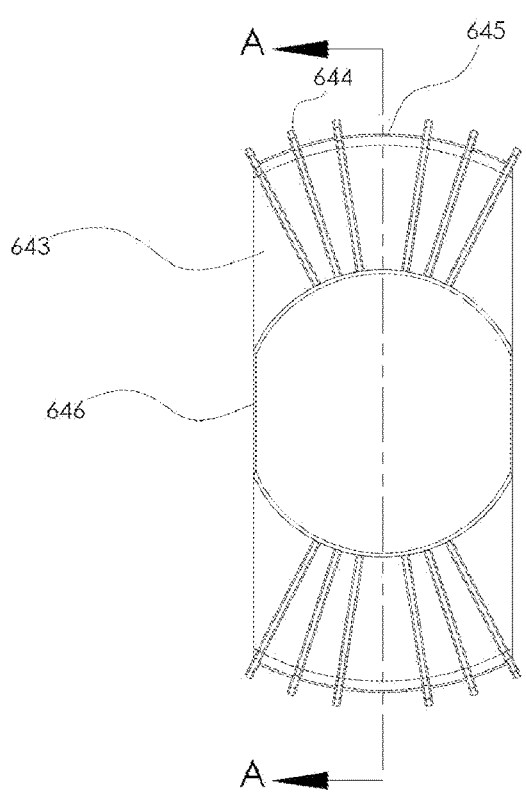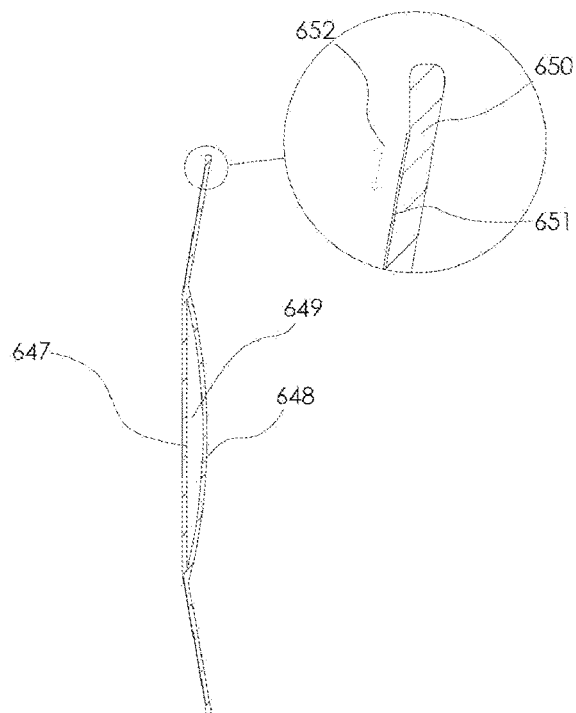
Fig. 6h          Fig. 6i
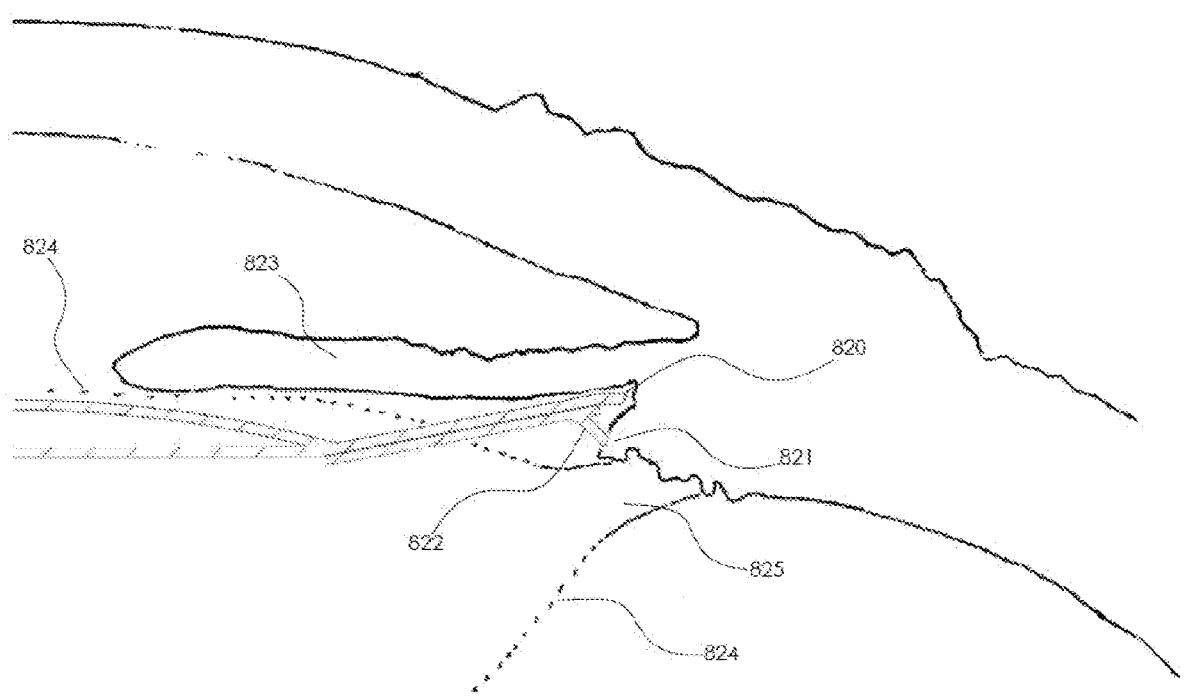
Fig. 8a

INTRAOCULAR LENS AND METHODS AND/OR COMPONENTS ASSOCIATED THEREWITH

TECHNICAL FIELD

Embodiments of the invention relate to intraocular lens and/or components such as haptics or the like that are associated and/or in coupling relationship with such lens.

BACKGROUND

Accommodation

Accommodation is the ability of the human eye to change its optical power, in order to focus on objects at various distances. This ability is gradually lost with age related changes in the eye, resulting in the patient using reading spectacles or other correction. This condition of the loss of accommodation is known as presbyopia and occurs to varying degrees in all humans, starting from around the age of 45 and lost completely by the age of around 65-70 years.

The principle of accommodation according to the Helmholtz theory, is that during distance vision, the ciliary muscle is relaxed and the zonular fibers that cross the circumlental space between the ciliary body and the lens equator are tensioned. When the neural impulse to accommodate the lens is given by the brain, the ciliary muscle contracts inwards radially and also moves forward anteriorly. This releases the tension in the zonules. The reduced zonular tension allows the elastic capsule of the lens to contract, causing a decrease in equatorial lens diameter and an increase in the curvatures of the anterior and posterior lens surfaces. Such changes in curvature are responsible for increasing the optical power of the lens and this enables focusing on near objects. When the ciliary muscle relaxes, the zonular tension on the lens equator rises back to its resting state. This increased tension on the lens equator causes a flattening of the lens, a decrease in the curvature of the anterior and posterior lens surfaces, and a decrease in the dioptric power of the unaccommodated eye.

According to Helmholtz, presbyopia results from the loss of lens elasticity with age. When the zonules are relaxed, the lens does not change its shape to the same degree as the young lens; therefore, presbyopia is an aging process that can be reversed only by changing the elasticity of the lens or its capsule. This theory is the most widely held theory today on accommodation.

Intraocular Lenses

Intraocular lenses (IOLs) are usually implanted in patients with cataracts. A cataract is a condition in which the natural crystalline lens has lost transparency, leading to various degrees of vision impairment. In the vast majority of cases today, cataract surgery involves removing the cataractous lens, and in its place an IOL made of a type of acrylic or silicone material is inserted or injected via a small incision in the outer surface of the eye. IOLs are typically placed in the capsular bag, the original anatomical location of the crystalline lens, or in the ciliary sulcus which is between the iris and the capsular bag.

Most IOLs implanted are monofocal and therefore most patients cannot rely on unaided vision for near activities such as reading. There is no accommodation as the natural crystalline lens has been removed.

The increase in knowledge and widespread effectiveness of cataract surgery, along with an ever growing and ageing population, has created a demand to increase both the predictability and quality of the visual outcome, in that the patient will need to rely less on spectacles or other forms of correction. This has also instigated several attempts to solve the problem of presbyopia.

The first types of IOLs in this regard to be commercialized were refractive bifocal and diffractive bifocal, trifocal and continuous-focus IOLs, which create multiple retinal images ranging from distant to near objects. While improving the patient's near and intermediate vision in comparison to monofocal IOLs, these multifocal IOLs cause various photic phenomena such as halos and glare in varying severities, and for diffractive IOLs, also diminish the contrast sensitivity at each focus.

The second type of IOLs, known as psuedoaccommodating IOLs, which by using various mechanical mechanisms, attempt to directly harness and amplify the force generated by the ciliary muscle to create dynamic changes in focus on demand, thus mimicking the natural youthful crystalline lens. These IOLs do not diminish the level of light reaching the eye from any given object, and do not overlay images on the retina from different focal lengths. This IOL type involves use of various levers and fulcrums, fluid filled cavities to decrease the rigidity of the lens assembly, use of dual optics or magnets. The drawbacks of these lenses are primarily that they either do not create the required amount of optical power change required for reading, or need to be implanted through a large incision thus creating iatrogenic corneal astigmatism.

The capsular bag, having been emptied of the crystalline lens, goes through a process of regeneration of lens epithelial cells, via mesenchymal cells migrating from the equator of the capsular bag, and fibrosis and contraction of the capsule itself. This changes the mechanical properties of the capsular bag and limits its viability to transmit mechanical forces to a psuedoaccommodating IOL. Ciliary muscle contraction during full accommodative effort reaches approximately 0.1 mm per diopter in terms of ciliary muscle ring diameter (Richdale et al; Invest Ophthalmol Vis Sci. 2013; 54:1095-1105). This value may be lower after cataract or refractive lens exchange surgery due to residual rigidity in the capsular structure that remains in place. However, it has been found that ciliary muscle movement increases after cataract surgery.

More recently, another type of lens has been described which uses electrical power to activate a lens made of liquid crystal substances, which then changes the refractive index of the lens, and thus inducing changes in the optical power. These IOLs do not effectively require any movement at all, but are currently not flexible and require delivery through large incisions.

Electroactive Polymers in Biomedical Implants

Polymers are used in various medical devices due to their biocompatibility, application-specific mechanical properties and relatively easier and cheaper manufacturing methods. Dielectric elastomers have been used in artificial muscle research, and provide very large elongations per unit of electrostatic force due to their softness and high Poisson ratio. Piezoelectric polymers have been used in active elements in biomedical devices, such as ultrasonic transducers and sensors.

Most of these devices are on the scale of millimeters, and incorporate additional components such as power sources which further increase the implant size. This being a relatively unexplored area, a seemingly great potential benefit lies in creating structures that utilize electroactive properties to maximize the mechanical displacement per the space available for the device. The goal would be to more efficiently create spatial displacements in structures and devices formed of dielectric elastomers or piezoelectric polymers, by way of inducing voltage at the external boundaries of such structures.

However, in order to create large relative strains which would be useful in a medical implant, large voltages are required. A solution could be in decreasing the thickness of an electroactive element, perhaps to micro- and nanoscale dimensions, as the electrical field across such an element is inversely proportional to the element thickness. In this way the strains may remain small but the cumulative displacement is large. Herein lies a possible obstacle as extremely small structures may not be practical to manufacture or create enough such absolute displacement. Still, there seem to be a number of unexploited tools on hand to overcome challenges in this field.

US2011/0142806 A1 describes use of electrospun piezoelectric polyvinylidene fluoride (PVDF) as a scaffold for stem cell culture and tissue engineering applications. However, the PVDF is not part of the final engineered tissue.

U.S. Pat. No. 5,522,879 A describes a structure of electrospun PVDF on a collector and can be used as a neural or vascular prosthesis.

In WO 2014/100259 A1, a piezoelectric polymer implant is disclosed that acts as a patch that undergoes flexure and treats the tissue it is attached to by heating, electrical signals or drug delivery.

U.S. Pat. No. 7,128,707 B2 Deals with electroactive polymers as artificial muscles or muscle patches, US2011/0152747 A1 discloses a medical device made of an electroactive polymer covered by a photovoltaic layer.

Piezoelectric polymers have also been described as energy harvesting devices. In US2011/0275947 A1 PVDF is used as a power source for a cardiac implant, utilizing the natural motion of the heart's contraction and expansion to create an internal voltage.

WO 2015/123616 A1 Discloses a vibration sensor for detecting motion in the ciliary muscle. The device is a thin film piezoelectric polymer mounted between a pair of electrodes on a silicon base in a cantilever structure.

US2014/0192318 A1 is an external device for detecting electric activity in the ciliary muscle.

US2014/0240658 is a sensor mounted on an ophthalmic lens that detects chemical or photonic stimulus, with a power source, power management circuitry, clock generation circuitry, control algorithms and circuitry, and lens driver circuitry.

US2007/0260307 A1 Describes an IOL that is actuated by a dielectric elastomer.

U.S. Pat. No. 8,834,566 B1 Describes an IOL with a pair of electrode rings that by attraction changes the curvature of a fluid medium sandwiched between two lenses, also creating axial translation. This method however may be limited in displacement as the electrodes do not cover a large area of the optic as they are not transparent or flexible.

One of the more promising methods for energy harvesting is the triboelectric effect. Two materials in intermittent contact with each other create contact electrification which passes charge from one to the other. A chemical bond is formed during the contact, and the electrochemical potential is equalized by the passing of charge between the materials by electrostatic induction. A similar process occurs during separation, although the charge is typically not the same as with contact. However, contact itself may not be necessary when one material is an electret, having a quasi-permanent charge and therefore allowing a charge to build up on an opposing conductor (S. Niu, Z. L. Wang, Theoretical systems of triboelectric nanogenerators, Nano Energy 2015).

US2014/0084748 A1 and US2014/0246950 A1 are examples of such triboelectric nanogenerators.

SUMMARY

The following embodiments and aspects thereof are described and illustrated in conjunction with systems, tools and methods which are meant to be exemplary and illustrative, not limiting in scope.

In an embodiment, there is provided an intraocular lens (IOL) comprising a clear optic and means for actuating change in curvature in at least a portion the clear optic.

In another embodiment, possibly combinable with the former embodiment(s), there is provided also an intraocular lens (IOL) comprising anterior and posterior portions, possibly multiple anterior and posterior portions, possibly clear optic portions, spaced apart by a cavity, possibly multiple cavities formed between any two said portions and each portion being at least partially formed from transparent material, and an actuator for urging change in curvature in at least one of said portions.

In a further embodiment, possibly combinable with the former embodiment(s), there is also provided an intraocular lens (IOL) comprising a clear optic and an actuator for urging change in curvature in at least a portion of the clear optic, wherein the actuator comprising a stack of electroactive material layers (EAMs) with interdigitated electrodes.

In yet a further embodiment, possibly combinable with the former embodiment(s), there is provided a haptics for coupling to an optic body of an intraocular lens (IOL) of at least any one of the former embodiments, wherein portions of the haptics comprise an energy harvesting mechanism.

In addition to the exemplary aspects and embodiments described above, further aspects and embodiments will become apparent by reference to the figures and by study of the following detailed descriptions.

BRIEF DESCRIPTION OF THE FIGURES

Exemplary embodiments are illustrated in referenced figures. It is intended that the embodiments and figures disclosed herein are to be considered illustrative, rather than restrictive. The invention, however, both as to organization and method of operation, together with objects, features, and advantages thereof, may best be understood by reference to the following detailed description when read with the accompanying figures, in which:

FIGS. 2, 2a, and 2b schematically show various embodiments of intraocular lens of the invention;

FIGS. 3a-3e schematically show additional embodiments of intraocular lens of the invention;

FIGS. 4, 5, 5a, 5b, 5c, 5d, 6, 6a, 6b, 6c, 6d, 6e, 6f, 6g, 6h, and 6i schematically show various components of intraocular lenses and/or haptic embodiments of the invention;

FIGS. 8a, 8b, and 8c schematically show possible arrangement of intraocular lenses and/or haptic embodiments in relation to elements of a human eye.

DETAILED DESCRIPTION

Electroactive Actuating Lens Element

Figure 1:
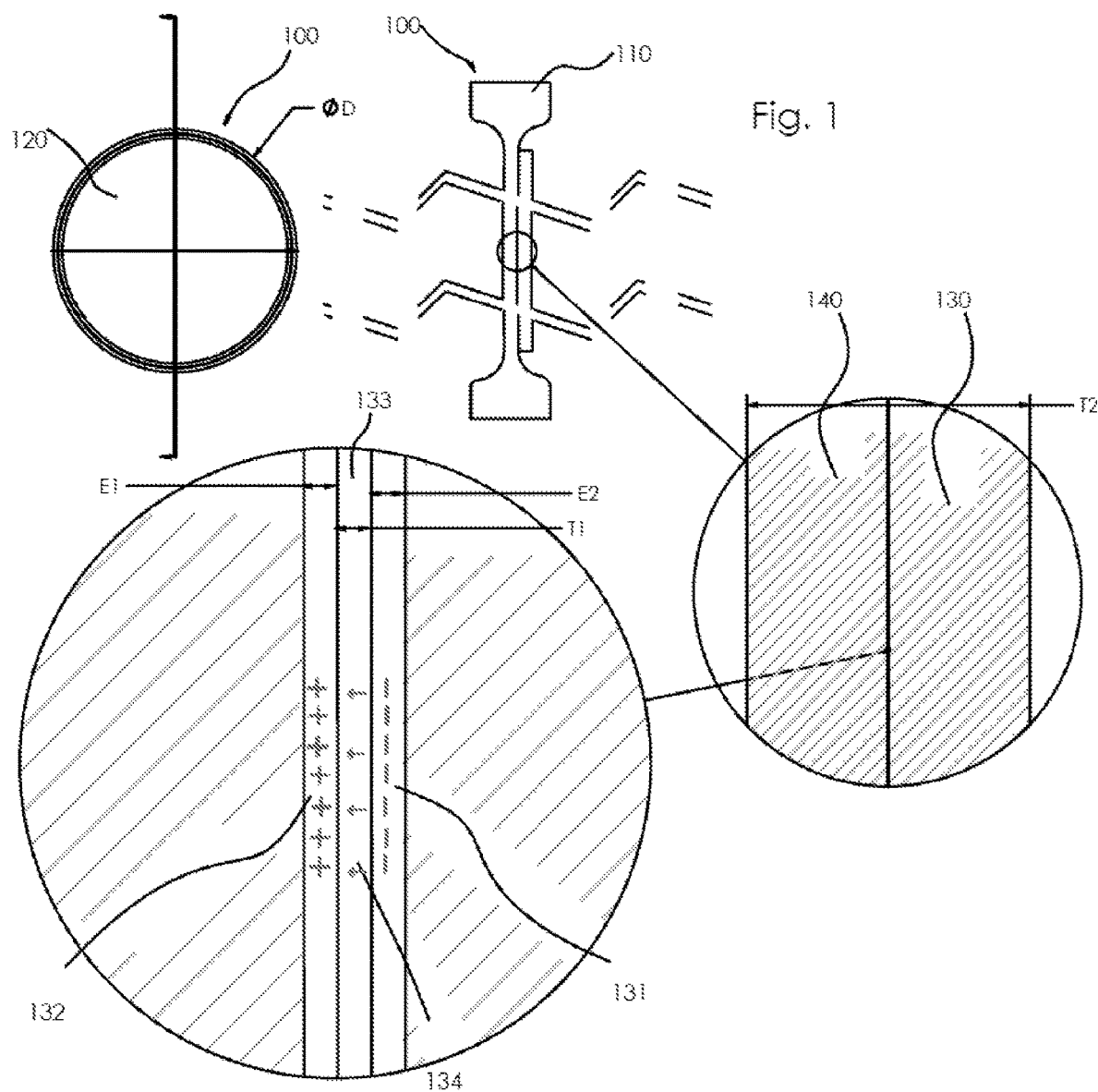
FIG. 1 schematically shows an embodiment of an intraocular lens of the invention.

In the first aspect, the present invention addresses the problem of presbyopia by an IOL, part of which consists of an optical lens element, made of optically transparent material. This transparent material may be piezoelectric or a dielectric elastomer.

In the discussion herein, the terms transparent lens element, optical lens element and membrane refer to the same component. Furthermore, in the various aspects of the invention discussed herein, the term transparent may refer to being optically transmissive to at least 90% of incident visible light.

A piezoelectric material deflects when an electric field is applied, depending on the direction of the field and the coupling coefficient of the material for the given direction. A dielectric elastomer is a passive, minimally compressible material, that when sandwiched between two compliant electrodes, can convert the electrostatic attraction or repulsion between the charged electrodes into mechanical energy. This is done by a change in the thickness of the layer. An in-plane strain is induced that changes the surface area of the elastomer.

When such an electroactive layer is formed with a directional bias in it, such as in a concave-convex or convex-concave lens, with a clamped boundary condition on the edge of the layer, the forces result in deflecting the layer in the direction of the bias.

The membrane of an electroactive material may be cast molded, injection molded, drawn or pressed from molded or extruded sheets and cut to size, electrosprayed or spin coated from melted granules or from solution on a substrate or any other suitable method to achieve thickness, poling directionality (in the case of a piezoelectric material) and transparency, such that is known to those skilled in the art.

The transparent lens element is in contact with one or both of its surfaces with an electrode.

In one or more embodiments, the electrode is transparent, and is in turn coated or connected to another transparent material of high refractive index or different refractive index to the transparent electrode layer and/or to the piezoelectric/dielectric elastomer element. The purpose of this layer is to serve as a pre-prepared substrate in the manufacturing process, and to increase the optical power at the interface between the surrounding aqueous humour and the lens assembly.

In another embodiment the transparent electrodes have a refractive index larger than the refractive index of the piezoelectric element.

The electrodes may also be opaque, and remain outside the clear optic diameter.

In another embodiment the electroactive material may cover a certain portion of the lens surface, so that the electroactive element is formed as an annulus. The diameter of the smaller inner circle of the annulus may be from 1 micrometer up to 6 mm (in which the deflection forces are created at the edge of the lens element).

In an aspect of the invention applicable to most embodiments, the electroactive material (EAM) and electrodes preferably cover a substantially full portion of the lens surface, and said EAM and electrodes being substantially transparent. Such full coverage preferably optimizes displacement of the actuator and consequently change in curvature of at least a portion of the clear optic and in turn optical power of the IOL.

FIG. 1 shows a basic example of an optic body 100. The optic body 100 includes a thick ring 110 at its periphery (shown in section, thickness may be between about 100-500 micrometers) which is attached to a lens 120 of the optic body. The lens (possibly including the ring) may be comprised of a transparent polymer (130, 140) similar to common intraocular lens materials, such as hydrophobic acrylic, hydrophilic acrylic, silicon or the like. In this example the transparent polymer is on both sides of an actuator, however in some examples the actuator may be formed or located on one outer side of one or more transparent polymers. In some examples, the actuator may form the clear optic lens 120 without any polymer such as polymer 130, 140 associated therewith.

Polymers layers 130, 140 at least in certain embodiments may serve as a pre-prepared substrate in a manufacturing process, inter alia, for purpose of increasing the optical power at an interface between the surrounding aqueous humour and the optic body (which may also be referred to as a lens assembly).

In one embodiment one or more of such polymer layer and/or substrate layer may comprise of a polymer shell or container that is filled with a fluid or soft gel that is relatively soft and compliant so that possibly it does not hinder movement of the actuator. The material of the polymer shell may be at least one of a hydrophobic acrylic, a hydrophilic acrylic, silicone or the like. The material of the fluid or soft gel within the shell may be an at least one of silicone oil, an elastomer such as: polydimethylsiloxane (PDMS) which may be optically transparent and soft.

The elastomer type used preferably has a relative high elongation (possibly above 100% as measured in room temperature) and low Shore Hardness (for example measured according to ASTM D2240). Alternative metrics of the material softness may include having a low Young's modulus. In one example, a low Shore Hardness may possibly be between about 10 [Shore 000] and about 100 [Shore 00], and preferably below about 70 [Shore 000]. In one embodiment, a lower limit for the Shore hardness may be chosen to be about 30 [Shore 000] so as to limit risk of the substance within the shell from being dispersed within the eye in an event where a breach in the shell is adversely formed.

The actuator may include electrodes (possibly at least partially transparent) 131 and 132 that are negative and positive, respectively; for example made of PEDOT:PSS. The actuator includes an electroactive material layer (EAM) 133 that in one embodiment is a piezoelectric polymer, also transparent, for example made of PVDF. In another embodiment the EAM 133 may be made of a dielectric elastomer such as polydimethylsiloxane (PDMS) or optically transparent and soft silicone elastomer. The elastomer type used preferably has high tear strength and elongation and a low Shore Hardness. The arrows 134 are a representation of the poling direction (if a piezoelectric material is used), in this case parallel to the direction of the electric field. Dimension T2 is the overall thickness of the lens 120, for example between 1 and 400 micrometers. T1 is the thickness of the EAM layer of 133, for example between 1 and 1000 nm. Possibly, the electrode thicknesses E1 and/or E2 may be up to 1 order of magnitude to T1. For example, for a T1 being 0.5 micron, E1 and/or E2 may have a thickness between 0.5 micrometers and 5 micrometers.

In the context of the present disclosure, a lens including and/or being associated with an actuator may be also referred to as an actuating lens.

The curvature of this lens can be changed by applying voltage between thin and transparent electrodes 131, 132 in contact with the EAM. The electrode material may be spread over the clear optic of the lens and then preferably may be transparent, or be in contact with different areas of the lens and then may not necessarily be transparent, such as when using silver nanowires/nanoparticles as electrode material.

The curvature changes are calculated via an eye model, which takes into account biometric parameters of the eye, published in literature and known to those skilled in the art.

Such an eye model may be the Navarro-Kooijman (Navarro R, Santamaría J, Bescós J. *Accommodation-dependent model of the human eye with aspherics. J Opt Soc Am A.* 1985; 2:1273-1281, A. C. Kooijman, "*Light distribution on the retina of a wide-angle theoretical eye,*" *J. Opt. Soc. Am.* 73, 1544-1550 (1983)), Liou-Brennan (Liou H, Brennan N. *Anatomically accurate, finite model eye for optical modeling. J Opt Soc Am A.* 1997; 14(8):1684-1695.), or any other eye model commonly in use in intraocular lens design by those skilled in the art.

Within the eye model a lens is defined to provide an effective focal length of approximately 0 Dioptres ("0D") in one state, and a higher optical power in another state, and so doing can provide a range of foci between the two states, in a dynamic fashion according to the voltage applied to the actuator. This higher optical power may be 2.5D, 3D, 3.5D, 4D or higher.

In FIG. 2, the left optic body 100 shows a cross sectional view of the body's lens curvature in resting state, or the "0D" state. This may be the situation before the voltage is applied. That is to say that in at least some embodiments after cessation of application of voltage, a lens curvature preferably elastically returns to its resting state, where in a case of dielectric elastomer based lens cessation may include discharging a voltage present across the EAM and in a case of a piezoelectric lens after cessation voltage decays across the EAM possibly with no assistance. The right optic body 100 represents the curvature in an actuated state, e.g. in a "4D" state, in which the lens is focusing the image from near objects onto the retina. When progressing along optical axis A the curvature of this lens may be convex-concave or concave-convex (as illustrated in the right body 100), and may change between these states during actuation. For example the resting state may be a convex-concave lens, and the actuated state may be a concave-convex lens or stay convex-concave.

Figure 2B:
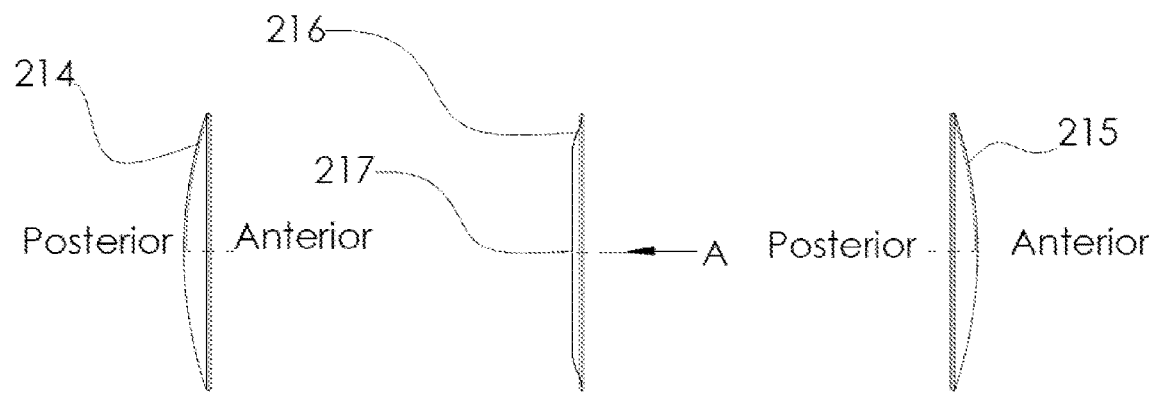

Flipping between convex-concave and concave-convex states (or visa-versa) may be achieved, for example in an embodiment of an actuator 1200 shown in FIG. 2a possibly combinable with actuator 120. Here actuator 1200 is embodied as comprising dielectric elastomer material. Actuator 1200 has anterior and posterior surfaces 1201, 1202. The figure illustrates a setting of a given polarity on an electrode 213 on at least a portion of one surface 1202 (posterior for example, negative), and opposing polarity on an electrode 212 on at least a portion of the second surface 1201. The bottom enlarged section illustrates a contact point 210 (anterior, positive) for providing electrical charge to surface 212. The periphery of here the anterior surface has in this example negative polarity on a separate electrode 211 shaped as an incomplete annulus, with the break around the positive contact point 210. Thus the posterior electrode 213 and the annular electrode 211 repulse initially, creating a flipping of the actuator's bias in its periphery in terms of deflection, shown in FIG. 2b. In a direction along optical axis A, the left state of actuator 1200 illustrates a concave-convex shape, just before being flipped. The middle state of actuator 1200 illustrates a flipped peripheral area 216 and a central area 217 which is flattening towards a flipped convex-concave shape as illustrated in the right state of actuator 1200 to result in a possibly fully deflected convex-concave shape 215. Flipping may be done gradually according to the accommodation demand. This is because the electrostatic repulsion increases the localized thickness of the elastomer in an annular section defined by electrode 211 thus creating an in-plane tensile stress on the central area of the lens, which pulls it taut into a flatter curvature.

In one aspect of this invention different ranges of maximal near vision correction may be suited to different patient needs. This may be done by evaluating the available range of motion occurring during accommodation for a given patient and tailoring the response of the actuator accordingly.

Far Vision Lens and Actuating Lens Arrangements

In another aspect a series of lenses may be defined within the eye model to describe a range of optical powers for far vision correction. In this case there may be a separate and independent lens defined to provide an effective focal length suitable for far vision correction, and another lens which is the dynamically accommodating lens that can change its curvature between the two states as described herein before.

Far vision correction includes rotationally symmetric and rotationally asymmetric optics such as in toric optics. The form of this far vision correcting lens may be biconvex, convex-concave, concave-convex, biconcave or any other form that may achieve the optical power required. The optical power required may be a small correction following other surgical procedures conducted on the patient's eye. Additionally the lens surfaces may be aspheric in such a way that controls the aberrations of the optical system, in any manner known to those skilled in the art.

Figures 3A, 3B, 3C:
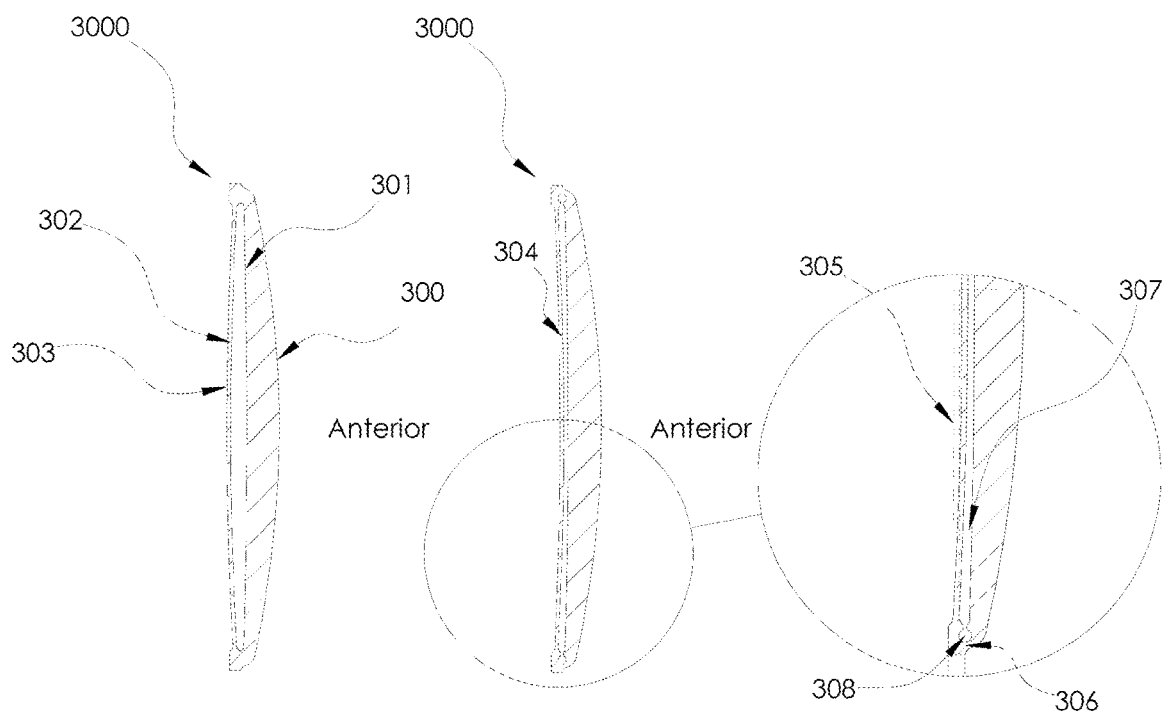

FIG. 3a shows an example of an optic body arrangement of convex and concave lens surfaces 300, 301 which provide the baseline optical power for far vision, in this example on the anterior side which is to the right of an optic body arrangement 3000. Possibly, the baseline optical power for far vision may be on the anterior side in order to avoid interference with the iris and/or pupil. Here the posterior lens surfaces are concave-convex 302,303. Alternatively as in FIG. 3b the posterior lens is convex-concave 304. Furthermore, the posterior lens may be connected to the far vision lens by way of a bridge or connecting feature 306, shown in FIG. 3c that is included or part of ring 110 shown e.g. in FIG. 1, which provides the necessary rigidity in holding the actuating lens in place on the optical axis. Between the lenses is a cavity 307 to prevent interference in movement of the actuating lens. The dotted profile of an actuating lens in the "0D" state is shown in 305 (see FIG. 3C). Bridge 306 may be provided with passages or fenestrations (see 550 in FIG. 5b) to permit fluid communication between cavity 307 and an exterior medium within the eye.

In one embodiment such a cavity 307 may be filled with a substance such as silicone oil or soft gel, having a different refractive index to the aqueous humour surrounding the lens, in order to allow for optical power changes that occur when radius of curvature is changed in the actuating lens. In the case of a cavity filled with silicone oil, to avoid leakage of oil into the aqueous humour, the passages in bridge 306 may lead to a fluid reservoir 308 allowing communication of the silicone oil from the cavity to the reservoir.

Such configurations are non-limiting and depend on the requirement of the patient, for example if the patient already has undergone cataract surgery and has an IOL in the capsular bag. In this situation a posterior concave surface may be desirable in order to avoid contact with the primary IOL, though if the deflection is small that may not be necessary. Furthermore the far vision lens may be of a lower dioptre, intended for small corrections as a secondary intervention. The far vision lens may of course also be the posterior lens in the arrangement. In another exemplary configuration, the lens is arranged to have an anterior lens for partial correction of far vision, then more posteriorly the near vision actuating lens, and then an additional more posterior lens for the remainder correction of far vision. This example has two cavities formed by three lenses. In this way the thinner near vision lens is protected by the far vision lenses from damage caused by handling on both of its sides.

Stacking of Actuating Layers

In another aspect an actuator according to certain embodiments of the present invention may include a stack of electroactive material layers (EAMs) with interdigitated electrodes that form a multimorph, to increase the possible deflection of the actuator and enable thicker individual EAM thicknesses and/or lower operating voltages. This is because a single EAM may be difficult to handle in manufacturing, and there may be a benefit in improved mechanical stability should the overall thickness of the actuator and/or lens be increased.

Figure 3D:
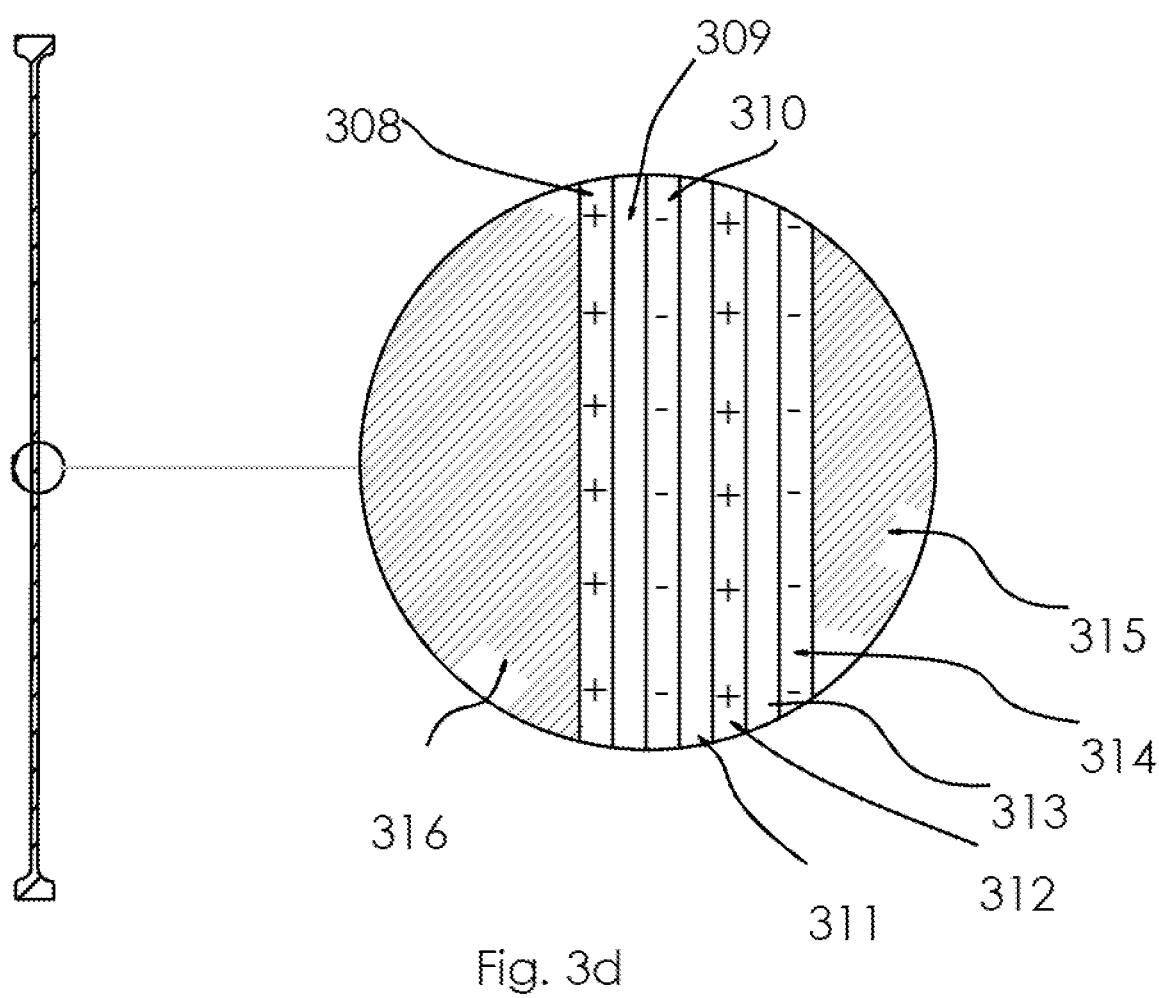

FIG. 3d shows a typical example of a plurality of layers comprising a multimorph. Electrode 308 is here a positive electrode, EAM 309 is a polymer element that may be a dielectric elastomer or a piezoelectric polymer. Electrode 310 is here a negative electrode. Then again EAM 311 is a dielectric elastomer or a piezoelectric polymer, electrode 312 a positive electrode, EAM 313 a dielectric elastomer or a piezoelectric polymer, and electrode 314 a negative electrode. Substrate transparent polymers 315 and 316 may be the materials typically in use in intraocular lenses, such as acrylic or silicone materials. In the case of dielectric elastomers the positive and negative electrodes in the figure attract electrostatically and compress the elastomer, creating an in-plane strain that increases the surface area and therefore creating a change in the curvature of the lens. The multiple layers of the multimorph cause an accumulation of strain that increases the curvature in an amplified manner for a given electrical field. The benefits may be the ability to decrease the required operating voltage and the ability to increase the thickness of the element, making for easier handling and less susceptibility to manufacturing defects.

Actuator Formed with a Dielectric Elastomer and Compliant Electrodes

For a single membrane of dielectric elastomer, sandwiched between two coated transparent electrodes, an overall thickness of $t_1$ can be defined, with $t_{el}$ being the thickness of each of the electrodes and $t_{mem}$ being the membrane thickness of the dielectric elastomer.

The in-plane stress $\sigma_{inpl}$ that causes the membrane to stretch and thus increase its surface area is defined by the electric field across the membrane E and the relative permittivity of the dielectric material $\varepsilon_r$. This is also known as the Maxwell stress:

$$\sigma_{inpl} = \frac{1}{2}\varepsilon_0\varepsilon_r\left(\frac{V}{t_{mem}}\right)^2,$$

Where $$E = \frac{V}{t_{mem}},$$

and V is the voltage. $\varepsilon_0$ is the permittivity of the vacuum.

For deflection of circular clamped plates, in the case where the deflection y is above half of the membrane thickness, a solution for stress $\sigma_{flex}$ is given by Roark's formulas for stress and strain (Seventh edition, Young and Budynas, McGraw-Hill ch.11 pp 448):

$$\frac{\sigma_{flex}a^2}{Et_1^2} = \frac{K_3 y}{t_1} + \frac{K_4 y^2}{t_1^2}$$

Where $\sigma_{flex}$ is the deflection stress, a is the outer radius of the plate, E is the Young's Modulus, $t_1$ the overall thickness of the plate, $$K_3 = \frac{2}{1-v}$$

(at the center or tne plate, v being Poisson's ratio of the material which is taken as 0.5 for a soft dielectric elastomer with compliant electrodes), $K_4$=0.5. The assumption that the plate is flat is a reasonable approximation, as the initial radii of curvatures are larger by 2-3 orders of magnitude (R>>a).

The deflection required is defined by the difference in the sagittal heights of the initial "0D" state when the actuating layer is at rest and the various actuated states which are achieved under different applied voltages ("XD", where the X indicates a certain dioptric value such as "4D"):

$$y_{XD} = \left(R_{XD} - \sqrt{R_{XD}^2 - a^2}\right) - \left(R_{0D} - \sqrt{R_{0D}^2 - a^2}\right)$$

Where $R_{XD}$ is the radius of curvature of a given state and $y_{XD}$ is the deflection at the given state. Here the non-limiting assumption of a spherical (rather than aspheric) surface is made.

Solving with given y values, known membrane dimensions $t_1$, $t_{mem}$, and a, with the known material properties of Young's modulus and relative permittivity, the voltage can be found that satisfies $\sigma_{inpl}=\sigma_{flex}$.

For multiple stacked dielectric elastomer membranes with interdigitating and compliant electrodes, a number of layers N may be introduced into the equation such that each layer reduces the required deflection of each individual layer, and correspondingly increases the overall thickness such that:

$$y_{XD_{individual\_layer}} = \frac{y_{XD}}{N},$$

and $$t_{1_{individual_{layer}}} = t_1 \times N.$$

The electric field E is unchanged for a given individual layer as the same voltage is applied as in the case of the single layer described above.

FIG. 3e shows an example of a simulation of a "4D" deflection of an actuating lens, in a paraxial version of the Liou Brennan eye model or substantially similar thereto. The actuation voltage that satisfies $\sigma_{inpl}=\sigma_{flex}$ is plotted against the individual layer thicknesses ranging from, in this example, 50 nm to 100 nm. Various numbers of layers N are used to show how increasing N may allow reduction of the actuation voltage and/or the individual layer thickness.

Actuator Formed with Piezoelectric Electrospun Nanofibers

In a further aspect of the invention, the EAM may be one or more piezoelectric micro- or nano-fibers. In one embodiment these fibers may be applied to the transparent electrodes on the substrate surface by electrospinning. The electrospinning may be accomplished by various methods such as near field electrospinning, air assisted far- or middle-field electrospinning or electrospinning using an auxiliary electrode to guide the fiber.

The objective in this case would be to create a pattern of the piezoelectric fiber on the surface in such a way that it can deflect in a manner that accumulates the deflection along the length of the fiber.

The fiber is electrospun in a way that maintains a fiber diameter that is similar to that of a single piezoelectric membrane layer as described above (1 nm to 1000 nm), but has improved poling directionality in that its poling extends along the fiber length, due to the electrospinning process. The poling direction is along the 3 direction which is parallel to the length dimension of the fiber.

Figure 4:
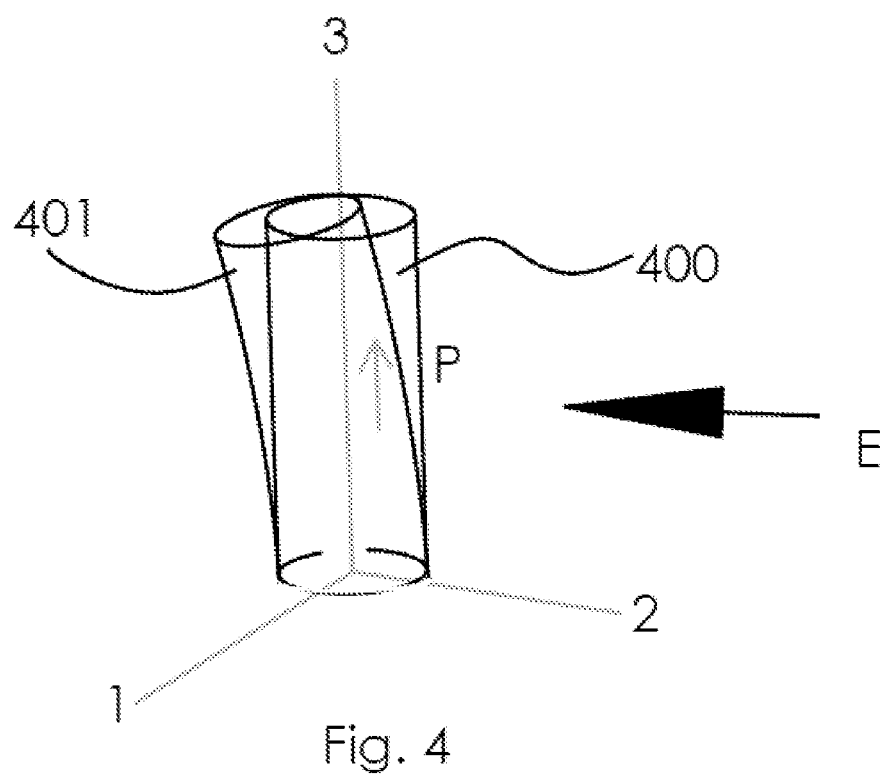

This further increases the size of the deflection vector in the desired direction. For instance as shown in FIG. 4, if the electric field direction E is transverse to the fiber 400 as in the 2 direction, a shear strain can be achieved, resulting in deflection as in 401 in the 2-3 plane. Deflection may be positive or negative depending on the sign of the coupling coefficient ($d_{24}$ or $d_{15}$) of the material selected.

Figure 5:
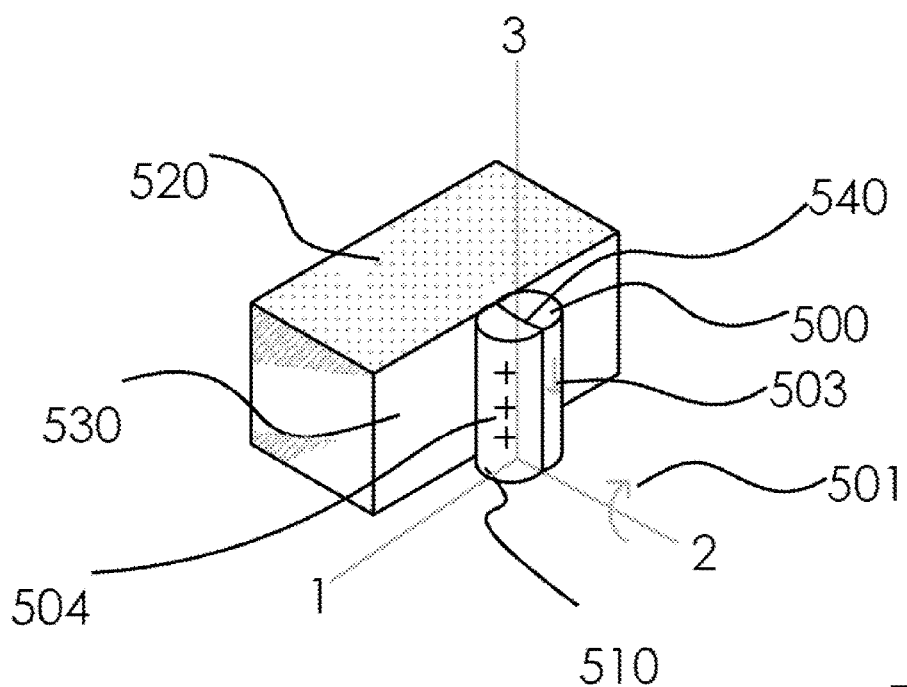

FIG. 5 shows a short segment of a pair of fibers 500, 510 deposited by side-by-side electrospinning onto the surface of a substrate 530 such as a transparent acrylic polymer. The piezoelectric material fiber 500 is electrospun together with an electrode fiber 510 such that an interfacial surface 540 exists between the fibers in order to create electrical contact. The electric field created by the charge 504 is in the "1" direction, and the poling direction is in the "3" direction (503). The strain in this case would be shear around the "2" axis as with 501. Again here depending on the sign of the coupling coefficient the direction of the strain about axis "2" is defined. The thickness dimension of the substrate 520 may be as described above (1 micrometer to 300 micrometers).

The electrode 510 may also be e.g. separately printed, rather than side-by-side electrospun.

Should the fibers be patterned as a continuous spiral as in one embodiment, such a strain may create a rotation around the 1 axis and would possibly create expansion in the radial direction of the element when voltage is applied. FIG. 5c shows an optic body 100, on which a spiral fiber is patterned. Shown in Detail A of FIG. 5c, the central region 575 of the optic body may be the starting point of the spiral deposition, with a first electrode or electrical contact point 573. The spiral is constructed in this example of a side-by-side electrospun piezoelectric material 571 and a transparent conductor 570 that is connected to the first contact point 573. The pitch of the spiral may be such that there is a gap between each spiral arm so that there isn't electrical contact between said arms. The poling direction 576 is shown.

The end point of the spiral deposition (shown in Detail B of FIG. 5c) may be again with the transparent electrode 570 being in contact with a second electrical contact point 572. The region of the substrate outside to where the spiral is deposited is also shown 574. By creating a voltage difference between electrical contact points 573 and 572, a deflection may be caused via the piezoelectric effect, accumulating over the length of the spiral.

In another embodiment the fiber is a hollow tube which further increases the ability of the fiber to deflect by increasing the coupling coefficient compared to the solid fiber (Cheng-Tang Pan, Chung-Kun Yen, Shao-Yu Wang, Yan-Cheng Lai, Liwei Lin, J. C. Huang and Shiao-Wei Kuo, "Near-field Electrospinning Enhances the Energy Harvesting of Hollow PVDF Piezoelectric Fibers," *RSC Advances* Vol. 5, pp. 85073-85081, 2015).

In another embodiment the fiber is coaxially electrospun with a transparent conductor as the core material.

In another embodiment the fiber is coaxially electrospun with a transparent conductor as a core and as and outer layer around the piezoelectric material.

In another embodiment, each spiral of side-by-side piezoelectric-conductor fiber (as shown in FIG. 5c) is encapsulated or partially encapsulated (with the electric contact points exposed), and spirals are deposited in a stack, forming a multimorph.

Figures 5A, 5B:
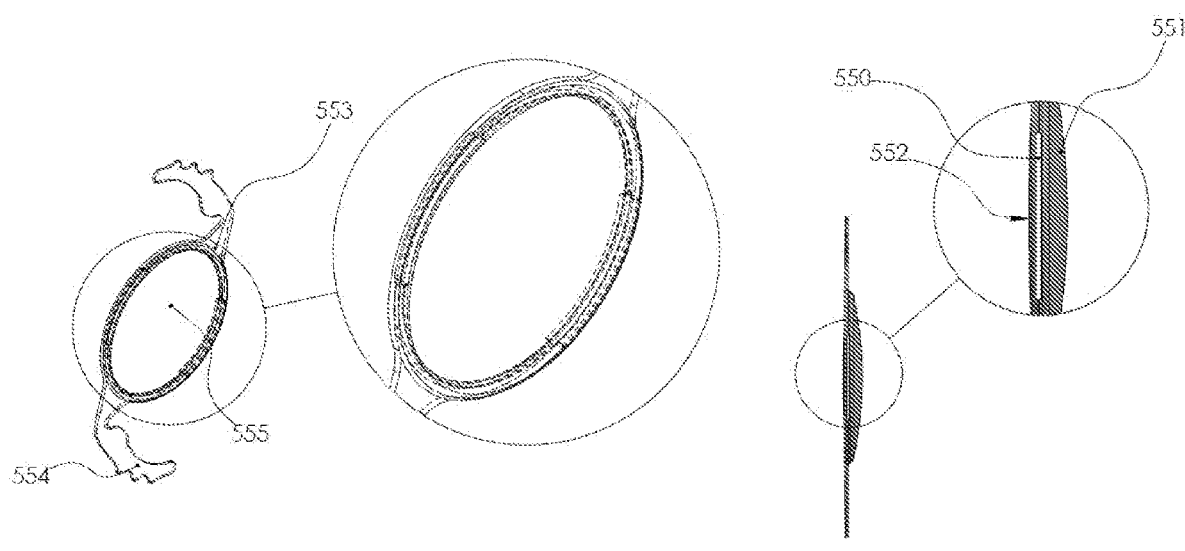
Figure 5D:
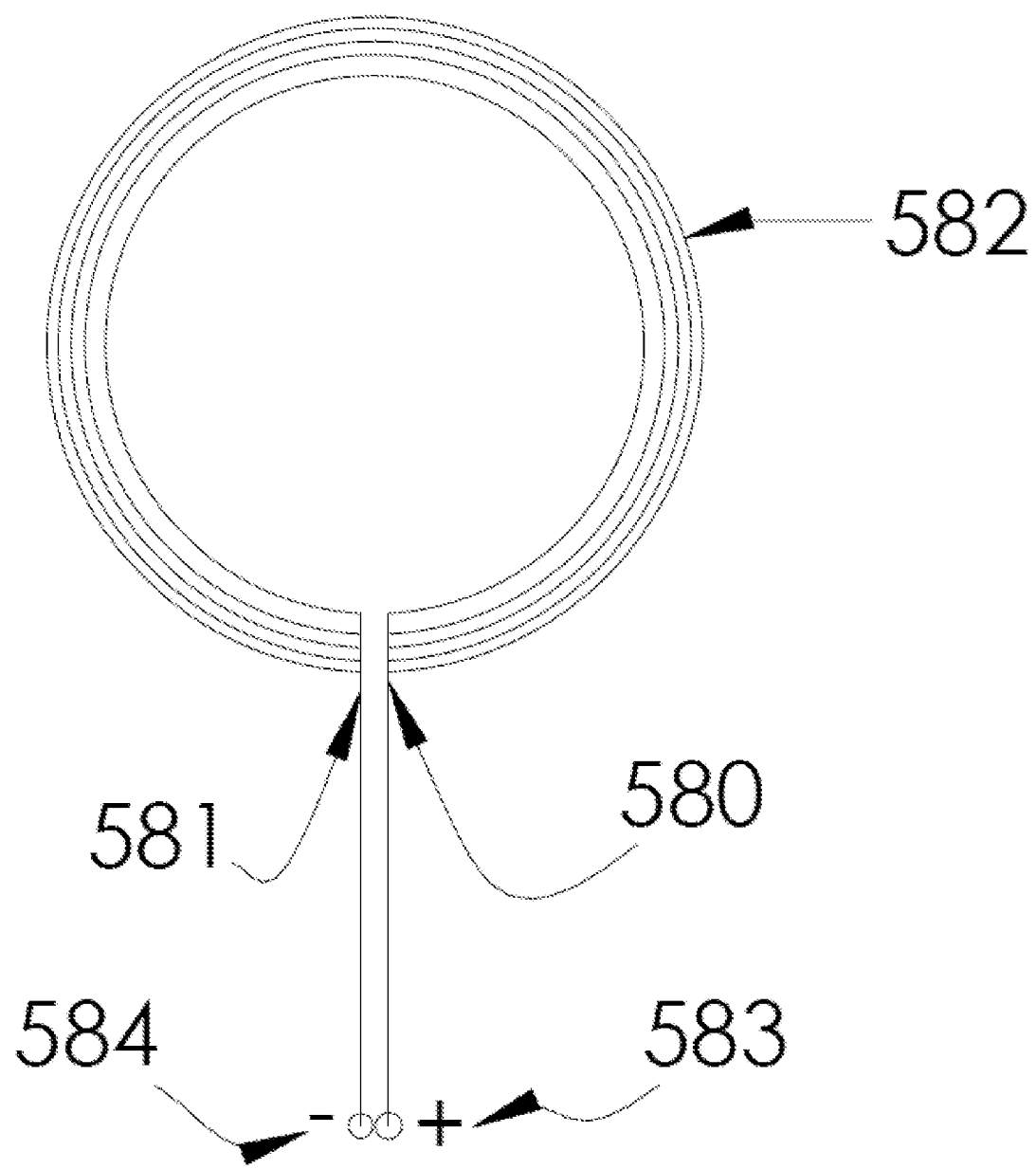

In another embodiment as shown in FIG. 5d, the pattern of a given electrospun layer is a set of concentric circles of fibers 582, each of which is electrospun side by side with a fiber of conducting material serving as an electrode (as shown in FIG. 5c), such that each fiber pair is deposited starting at one segment of the lens 580 and ending at another segment 581. Outside of the lens clear optic may be a positive 583 and negative 584 electrode, to which the start 580 and ending of the fiber pair 581 are in electrical contact with Structural Overview of a Device With attention drawn to FIGS. 6 to 8, aspects relating to various embodiments of haptics combinable with the various embodied optic bodies of the invention will be discussed.

Haptics continue from the optic body towards the equatorial contact area, either with the ciliary sulcus or in the capsular bag.

There may be various openings or fenestrations created in the periphery of the body (e.g. in ring 110 and/or bridge 306 discussed above and/or in adjacent regions thereto) to allow for the aqueous humour to penetrate into a space (e.g. cavity 307) between two lenses of an optic body (e.g. body 3000). This may be beneficial for manufacturing reasons and also to avoid having an additional material in this space which increases the overall bulk.

FIG. 5a shows a C-loop design haptic 554, wherein the optic body 555 is fenestrated on its periphery. The optic-haptic junction 553 provides support between the haptics and the two lenses in this example, as shown in FIG. 5b an anterior lens 551 and a posterior lens 552. Fenestration 550 is illustrated in the enlarged section of the view in FIG. 5b (being a peripheral view)

Piezoelectric Motion Sensor and Haptics

The motion of the ciliary muscle is generally characterized into two signal types, namely a high amplitude, low frequency set of signals of below 1 Hz that correspond to the main contractions and expansions of the ciliary muscle (i.e. accommodative responses), and range of low amplitude, higher frequencies, that correspond to various background muscle responses. These may be for example reactions of the body to fatigue; caffeine; fluctuations in intraocular pressure; adrenaline or constriction of the pupil as a reaction to ambient light changes. Small perturbations in the eye motion or saccades may also be a cause for high frequency motion of the ciliary muscle.

In an aspect of the invention, a motion sensor may be incorporated in the haptics. This motion sensor may have a multiple role in that it detects motion of an accommodative response, of various amplitudes depending on the accommodative stimulus, and also in detecting small motions at higher frequencies that the muscle undergoes constantly.

Figure 6:
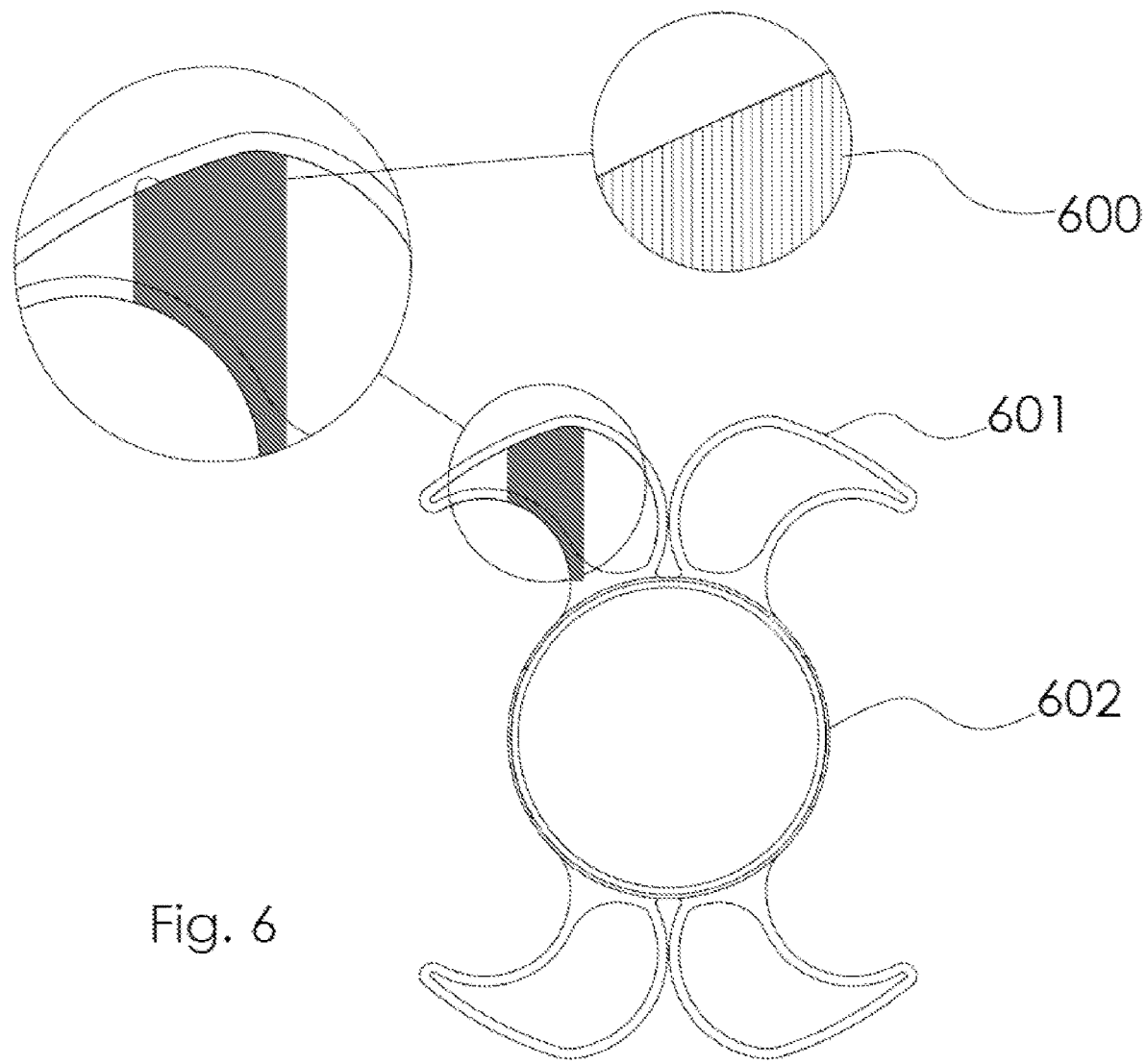

Shown in FIG. 6, is an embodiment of a motion sensor 600 comprising in this example a plurality of highly aligned fibers (forming a fiber array) of piezoelectric polymer, included in a haptic 601 which is connected to an optic body 602 (sensor is here illustrated being included in one of the haptics, however sensor 600 may be included in more than one in this example possibly in all haptics of this 4-loop haptic design that is shown).

Figure 6A:
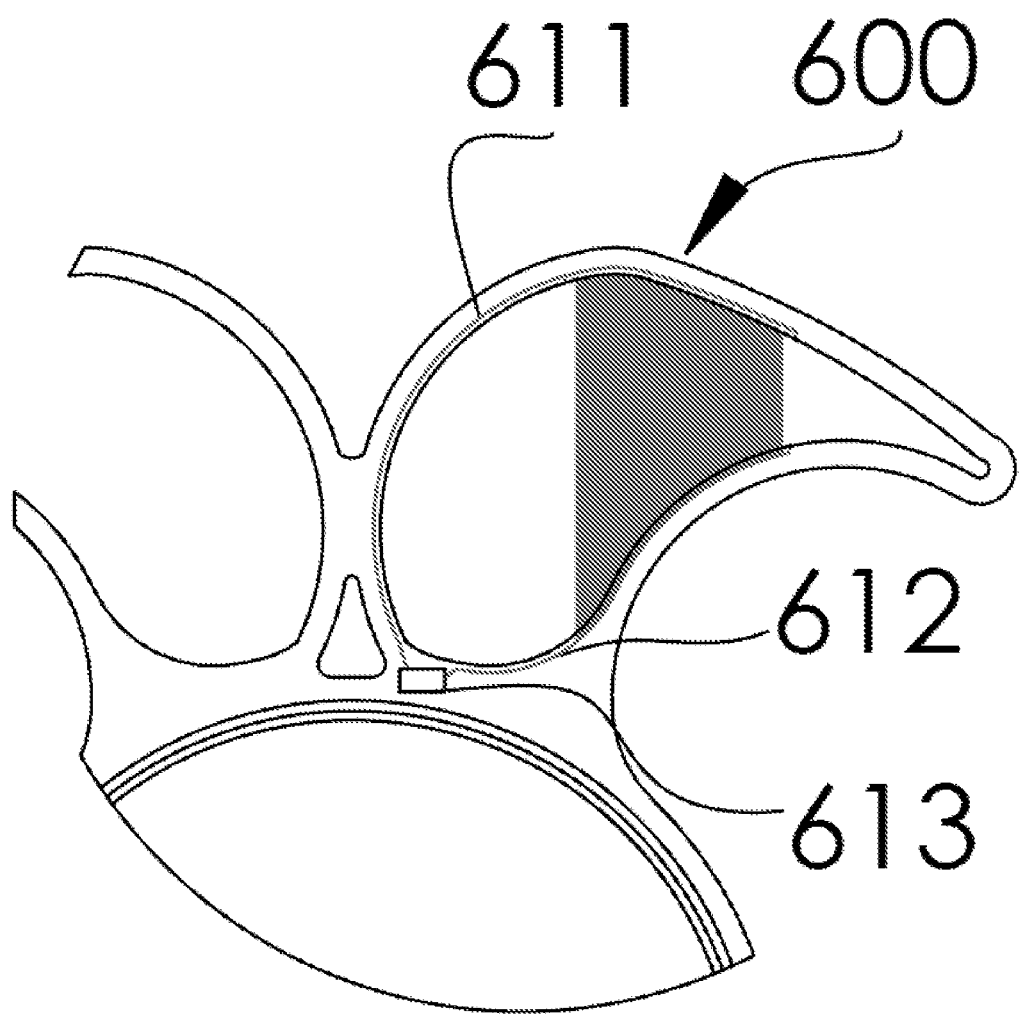
Figure 7:
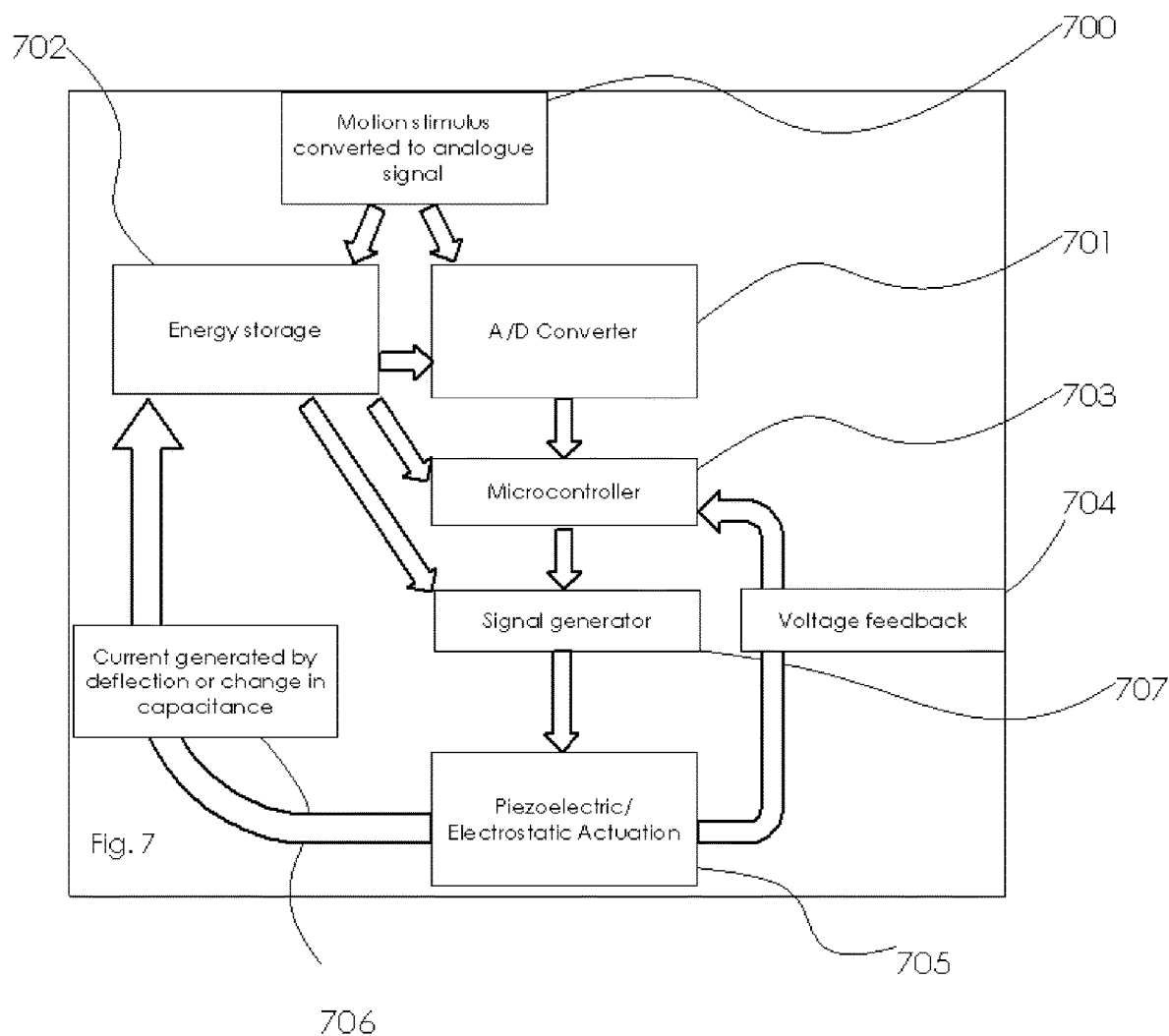
FIG. 7 schematically shows a flow chart illustrating various possible components of intraocular lenses and/or haptic embodiments of the invention.

In FIG. 6 and in the enlarged section in FIG. 6a, sensor 600 is illustrated accordingly including a plurality of highly aligned fibers of piezoelectric polymer, in connection with two electrode vias 611 and 612 that communicate with a control unit 613, with various components a possible embodiment of which is shown in the flow chart in FIG. 7. The motion of ciliary muscle applies force on the haptic loops in contact with it, and creates in the sensor embodiment 600 a possible buckling, bending and/or shear force on the fibers. This induces a voltage across the fibers, either high enough for overcoming a threshold required to induce motion in the actuating lens and/or to harvest energy to maintain the actuated state.

Figure 6B:
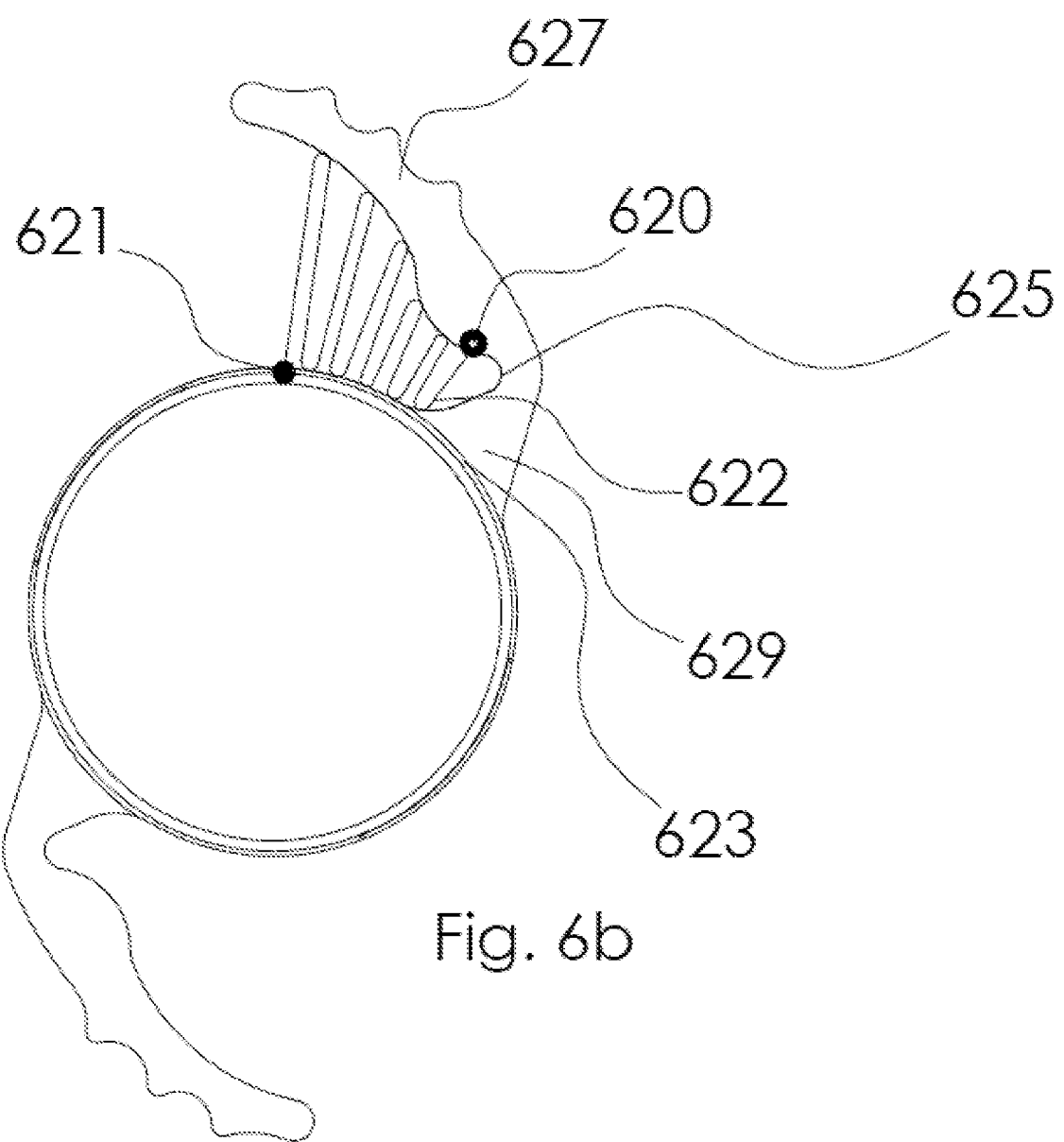

In an embodiment, motion sensor 600 may also take the form of a plurality of fibers deposited on a thin substrate, either on the haptics as seen e.g. in FIG. 6 or bounded by the haptic and the optic body as seen e.g. in FIG. 6b where that the fibers may possibly be formed in a "serpentine" shape zig zagging continuously back and forth between the haptic and optic body. The direction of the ciliary muscle movement, especially the circular muscle fibers which are sphincteric, is mainly in-plane with the haptics and radial, and thus the direction of the sensor fibers is preferably along this radial direction.

The electrospun piezoelectric material may form a single fiber or a bundle of fibers, either twined, braided or in parallel.

FIG. 6b shows an example of an exaggeratedly sparse (for illustrative purposes) serpentine electrospun fiber (or fiber bundle) 622, connected between the haptic and optic body (shown on just one of the sides of the lens), and having two electrical contacts at 620 and 621. The serpentine shape may be deposited by a CNC-type outline motion along the profile of the haptic and optic design outline. In an embodiment, the fibers may be deposited on a thin substrate, and then either removed as a sacrificial layer once the fibers are deposited thickly enough to support their own weight or left in place.

The piezoelectric material may be electrospun side-by side or coaxially with a conducting material, or as a composite material such as PVDF-TrFe, PVDF/Graphene Oxide, and PVDF/MWCNT. This may increase the n-phase content of the material, and reduce the fiber diameter, as is known to those skilled in the art.

The fiber of the motion sensor may cover any portion of the haptics either in addition or instead of the forms shown above.

In an embodiment of the present invention, haptics, which are the continuation of the optic body which holds the optical elements, are described. These haptics are shaped in a way that mechanically supports the optic body and maintains the axial position of the entire lens, as well as its centered position on the optical axis. At the same time, at least a portion of the haptics should be flexible in order that they fold or bend, at first for the delivery through the small incision in the cornea or limbus, and enough that the energy of the ciliary muscle be transmitted to the motion sensor.

In various embodiments, the entire haptics are shaped in the common or modified C loop type shape, 4 slotted or unslotted loops, 3 slotted or unslotted loops, slotted or unslotted plate haptic, such that is known to those skilled in the art.

In some embodiments the haptics are formed (possibly from an acrylic or silicone material or the like), to be thicker in a base close to the optic body of the lens in order to prevent unwanted deformation of the optical structures of the lens, caused by eye movements or ciliary muscle movements. Alternatively or in addition, the thickness may be maintained substantially similar as in the base or change according to design considerations and in addition a geometry may be employed that moves a flexure point of the haptic to a certain distance from the optical structures of the lens. For example, in the embodiment seen in FIG. 6b, a flexure point 625 is illustrated distanced from a base 623 to form a resilience region at a vicinity of point 625 about which an arm 627 of the haptic more distal from the optic body may be movable in relation to a leg 629 more proximal to the optic body.

In an embodiment, a fiber array such as fiber 622 (or equally fiber 600 seen in FIG. 6a) may be formed beyond flexure point 625 in a region of the haptic (e.g. arm 627) to sense motion in a region of the haptic more susceptible to motion.

Figure 6C:
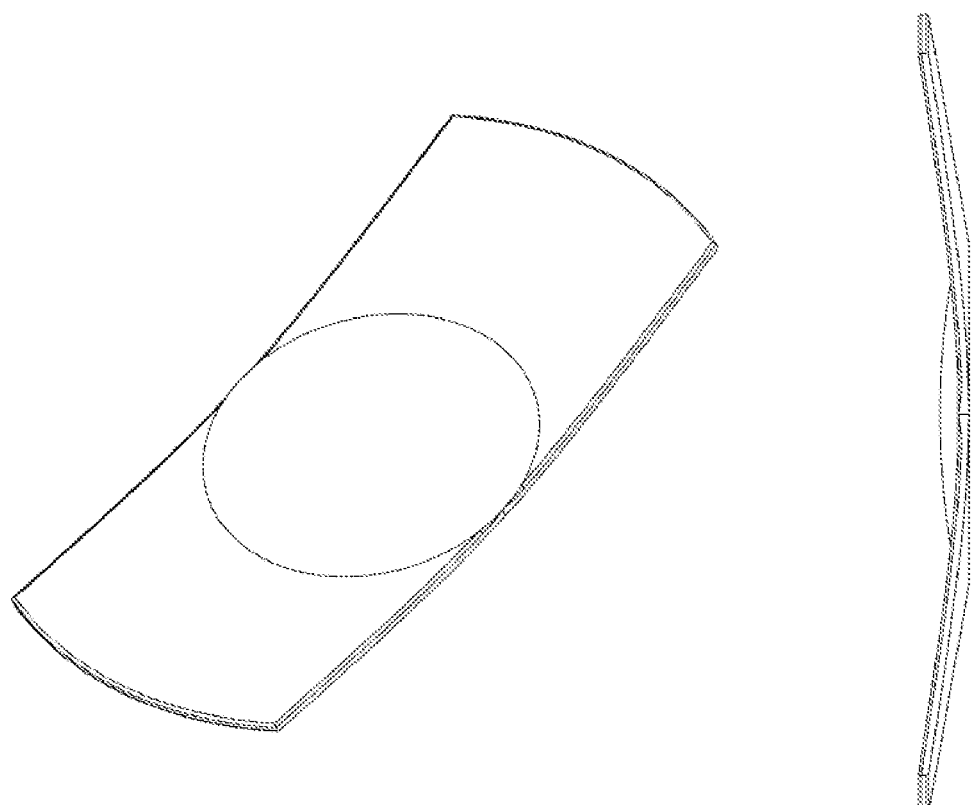

FIG. 6c shows haptics that are angulated in order to avoid iris chafe, a common risk for sulcus placement of planar or zero degree angulation IOLs.

In haptic embodiments including a slot (seen e,g, in FIG. 6) the fibers may accordingly be deposited across the slot, so that ciliary muscle movement creates a buckling in the fibers and a resulting current in the electrodes at each side of the slot. Alternatively instead of a slot some haptics may be formed in a zigzag or Z shape (not shown), and the piezoelectric fibers may be deposited across the gaps between the haptics in a radial direction. In another embodiment the piezoelectric fibers are deposited along the shape of the haptic (possibly along a contour of the haptic) instead of and/or in addition to just across the gaps. In this way the fibers also react to deflection modes other than buckling. In this embodiment each fiber has either a pair of electrodes at each of its ends, with or without a side by side, coaxial or core-and-shell electrospun electrode.

In another embodiment the sensor is a piezoelectric thin membrane or multimorph stack of membranes that are coated on the haptics with interdigitating electrodes, and thus harvesting multiple modes of forces applied by various movements of the eye and the ciliary muscle in particular. The membrane may also be formed across gaps between the haptics as contiguous single or multilayer membranes or formed as strips of the same.

In another embodiment the haptics themselves are formed of electrospun fibers (as described above, in an aligned or non-aligned manner), possibly onto a flexible conducting substrate, such that the concentration of sensors or harvesters is greatly increased. Increasing the concentration of the harvester units improves the yield of the energy gain per unit volume. This is done by reducing the spacing between fibers to pack them into a smaller surface area per fiber (i.e. to form a 3D haptic structure created from adjacently deposited fibers with substantially limited spacings therebetween). Fibers may be deposited in individual line segments or be continuous in a raster or zigzag shape (inter alia on the anterior and posterior surfaces of the haptic), or in a bending beam transduced configuration (on the plane of the haptic normal to the direction of movement of the ciliary muscle).

Such fibers may be deposited by mounting of the electrospinning syringe, spinneret or tip onto a 5 or 6 DOF robotic arm, or onto a 5 axis machining center such as a mill, or by mounting the syringe on a linear slide and the substrate haptic onto a 4 axis (3 axes and one rotating axis). The haptic would need to be between the spinneret or syringe or tip and a grounded electrode. In this way several layers may be deposited. Fibers in this case serves as a simple example, as by changing the dimensions and shape of a spinneret, different cross-sections of electrospun material can be formed such as ribbons.

Alternatively the electrospun fibers or membrane may be deposited directly onto a mold and then the haptic would be overmolded and in this way also encapsulate the fibers.

Encapsulation may be a requirement to prevent leakage current due to contact with the aqueous humour.

Triboelectric Energy Harvesting and Motion Sensing

The energy harvesting mechanism may in a further embodiment utilize the triboelectric effect, or contact electrification. Different materials have different charge affinities, and are ranked in a triboelectric series. Contact between materials on the positive end of the list with a material on the negative end of the list passes charge between them and can be stored in a capacitor or battery. It has been proposed that unequal effective work energy levels of the materials enable an extraction of electrons by the Schottky and/or tunnelling effect, from the energy level of one material to the other. A general rule has been proposed that for two materials, the material with the higher dielectric constant will become positively charged when contact occurs between the two materials. Others have suggested that ions rather than electrons are transferred for some materials.

In some embodiments of the present invention, a suitable pairing of different materials may be compressed or rubbed against each other by (for instance) the relaxing ciliary muscle, such that the friction or adhesion force, and subsequent separation force during the contraction of the muscle, create a periodic electrification of the materials.

The necessity of mechanical contact between the materials may be avoided by use of materials with electret properties such as fluoropolymers (examples of which may be polytetrafluoroethylene, fluorinated ethylated propylene or perfluoroalkoxy alkane). In such materials, surface or space charge storage is possible and can be maintained over long periods of time, thus frictional charge transfer between materials may not be necessary for electrostatic induction.

A negative charge affinity material such as positively poled β phase PVDF, positively poled β phase PVDF-TrFe, PDMS, PET, PTFE, FEP and a positive charge affinity material such as PHBV, negatively poled β phase PVDF, negatively poled β phase PVDF-TrFE, Nylon may be used as non-limiting examples.

Conductors on the ends of the opposing materials direct the current to storage components (such as component 702 of FIG. 7) and an A/D converter such as convertor 701. In some embodiments, the energy harvester may itself serve as a storage component.

The negative and positively charged materials are preferably encapsulated so that the aqueous humour, which contains electrolytes, is not in contact with the energy harvesting components. The electrolytes may discharge and/or mask the surfaces, preventing their efficient function.

The larger the surface area of the contact, the better to increase the transferred charge. In one embodiment the two surfaces in contact are comprised of electrospun fiber mats, either randomly deposited or aligned. The mats may be deposited on a conducting substrate such as PEDOT:PSS or any other conductor. Alternatively the surfaces may be thin films, micropatterned to increase the surface area. This can be achieved by creating a mold with high roughness and casting a material into the mold. The mold can be a metal mold treated by hydrochloric acid for example, and the cast material can be PDMS, fluoropolymer dispersions or PVDF. Transparency is not a requirement in the haptic area.

Since the energy harvesting component is hermetically sealed by its encapsulation to avoid contact with electrolytes in the aqueous humour, metallic conducting materials with higher conductivity may be used, such as silver or gold pastes, coatings, nanoparticles or nanowires or the like.

A relatively more rigid (though still flexible and foldable) substrate may support the energy harvester components, against which the ciliary muscle force may be applied. This rigidity directs the majority of the strain to driving the components together so that the maximal energy output is achieved.

Figure 6E:
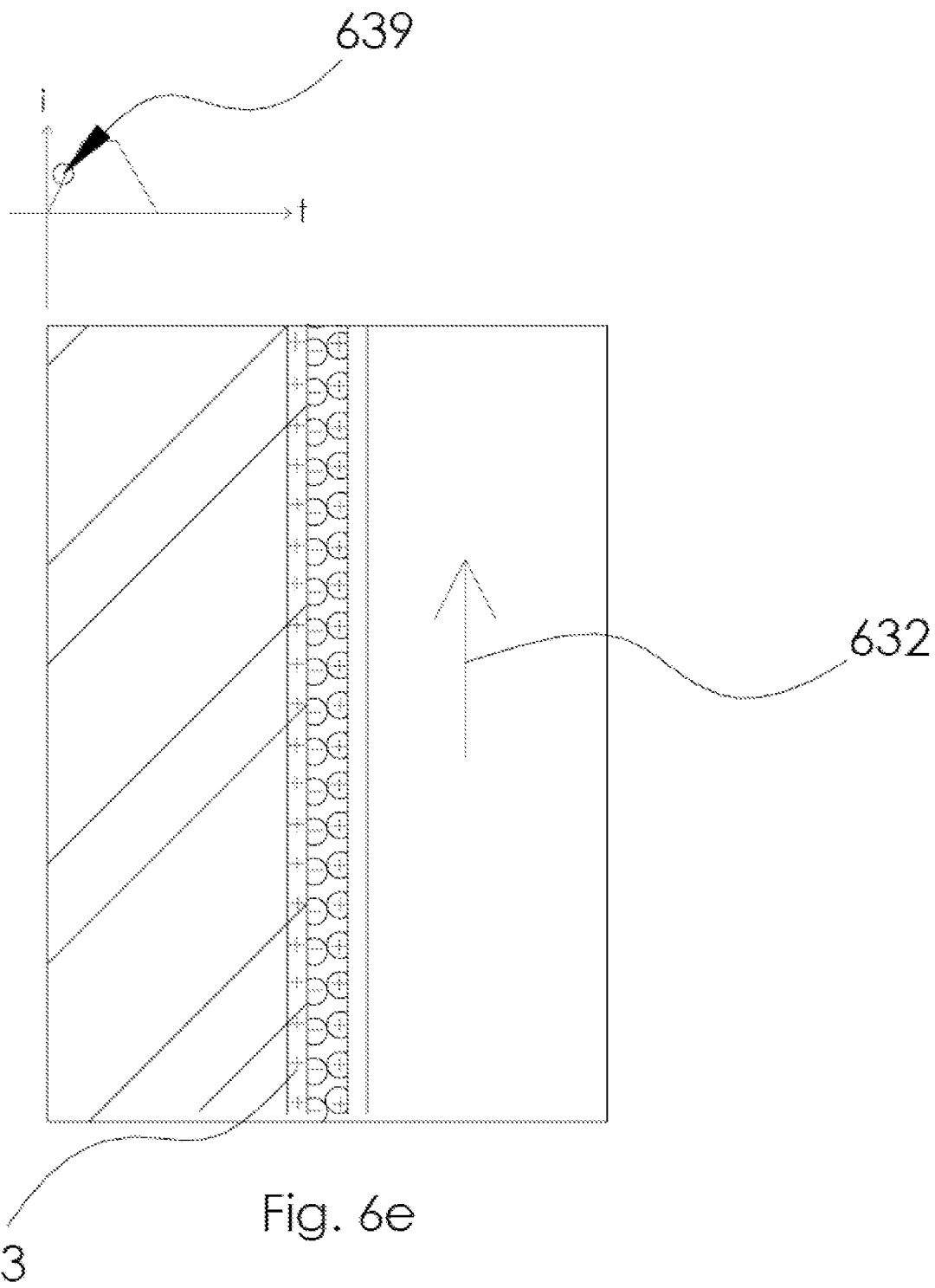
Figure 6F:
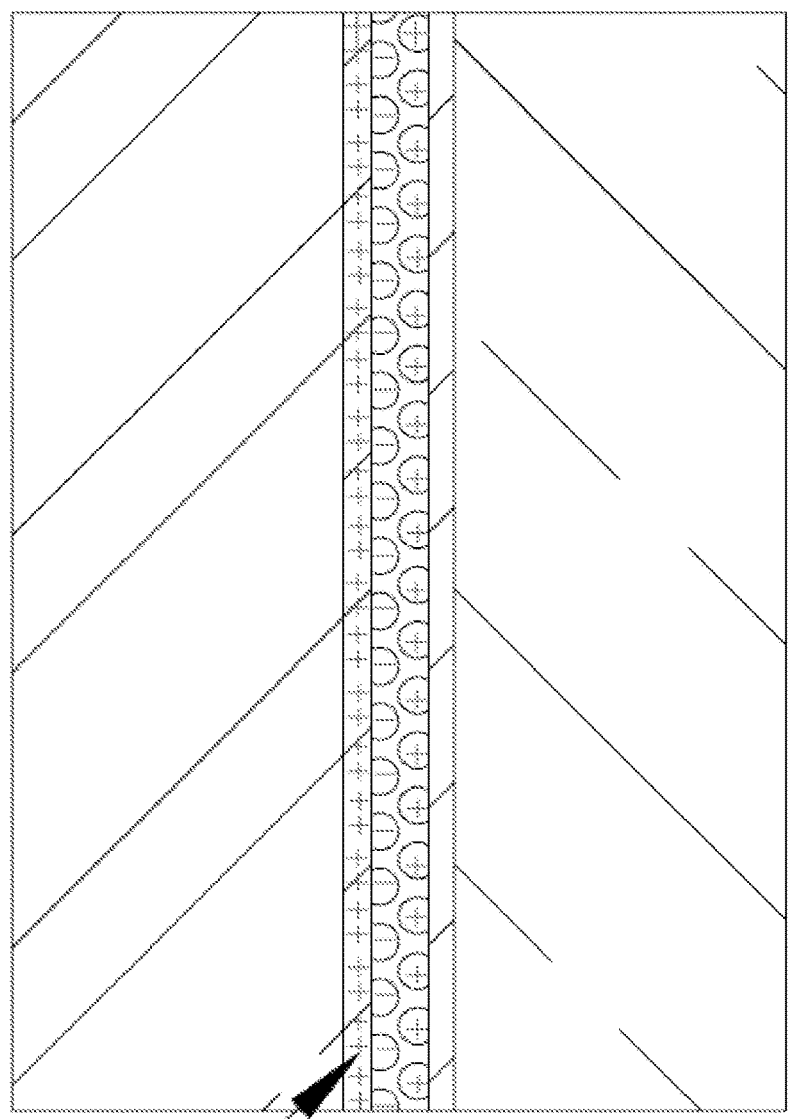

FIG. 6*d-f* show a triboelectric generator in cross section. Substrate material 634 on the anterior side of the haptics serves as a stator in order to avoid iris chafe. A moving substrate 633 on the posterior side, serving as a mover, may move e.g. in the direction specified by the arrow 632. The entire assembly fitting in the sulcus may in one example be between 50-250 micrometers thick.

Between the two mentioned layers 634, 633 may be located conducting layers or electrodes 635 and 636 on the posterior and anterior sides, respectively. Each layer 635, 636 may be deposited with nanostructures (possibly electrospun nanofibers or other nanostructures possibly formed by casting in a mold) of negative and positive affinity materials with different placing on the triboelectric series. For example, a negative charge affinity material 637 may be e.g. an electrospun PVDF fiber or a fluoropolymer electret, and a positive charge affinity material 638 may be e.g. at least one of PEDOT, PEDOT:PSS, PET, Nylon, Silver nanowires.

In FIGS. 6*d* to 6*g*, movement is shown for one small perturbation on the order of the diameter of the fibers. The movement may cause electron tunnelling from the energy level of the negatively charged 637 to the positively charged 638 material, creating a positive charge 653 on the anterior electrode 636. In FIG. 6*d*, the negative charge affinity material 637 may come in contact with positive charge affinity material 638 and transfers electrons to it. A net positive charge in the negative charge affinity material is caused and a net negative charge in the positive charge affinity material. Since momentarily the two surfaces 637 and 638 are in full contact over their surfaces, the overall charge is balanced and the current is substantially zero.

When a lateral force in the upward direction 632 (as shown in FIGS. 6*e* and 6*f*) is exerted on the mover, a separation is gradually caused between the negative and positive charge affinity materials, with a gap forming between the nanostructures on both sides of this gap. The charges that were transferred are retained in each material, as they are insulating materials. Now that the surfaces are no longer in contact, an electric potential is formed between the electrode layers.

Current is proportional to changes in the voltage over time as is known to those skilled in the art. The graphs above each respective FIGS. 6*d* to 6*g* schematically show the current 630 at each point in time. The load between the electrodes that forms part of the energy harvesting circuitry described previously is not shown for simplicity.

As described above, the current 631 in FIG. 6*d* is zero when there is no voltage change caused by no movement.

Figure 6G:
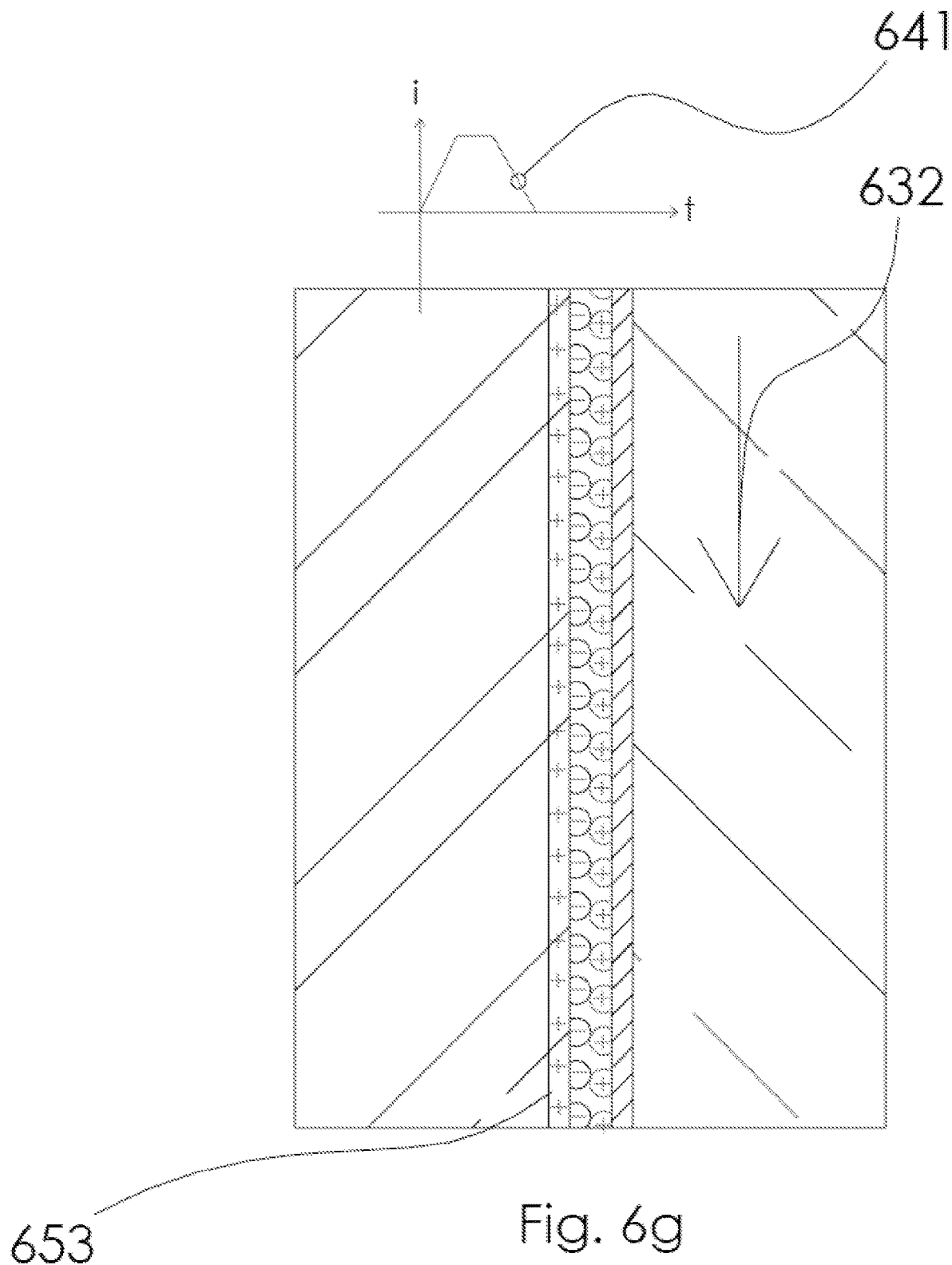

Next, in FIG. 6e, movement as in the direction shown by the arrow 632, the current 639 is becoming larger as the contact area decreases towards full separation in FIG. 6f, and maximal current 640. FIG. 6g shows the current decreasing 641 as the contact area once again gradually increases and the overall charge is eventually balanced at full overlap. Thus an alternating current is created.

Alternatively, in another embodiment, one of the materials 637 or 638 may be a conducting material, possibly with a different placing in the triboelectric series than the opposing insulating material. For simplicity, the negative charge affinity material. The charge imbalance described above in which the charge is retained when the materials come out of contact, is reduced due to the conducting nature of the negative charge affinity material, and the current returns to zero at this point. In essence, the harvesting frequency is effectively doubled in this arrangement. In addition, the construction of the electrode-insulator-electrode arrangement of this embodiment may be simpler to manufacture compared to the electrode-insulator-insulator-electrode arrangement described above in the previous embodiment. In the case of an electret material used as one of the materials 637 or 638, when the ciliary muscle reaches maximal displacement at full accommodative effort, it may be preferable that there be maximal overlap of materials to maintain a constant DC electric potential in order to maintain an actuated state of the lens.

FIGS. 6h and 6i are non-binding examples of an embodiment of a possible form the lens may take with an integrated triboelectric energy harvesting mechanism on the haptics, in this case plate haptics. The angulated haptics 645 are in contact an optic body such as above described embodiments 100, 3000, optionally comprised of an anterior lens 648, a posterior lens 647 and a cavity filled with aqueous humour 649 that can enter via a fenestration 646. The optic body, although described with respect to an optic body arrangement (such as arrangement 3000), may also be a single lens arrangement such a single actuating lens such as in optic body 100.

Mounted on the haptics and encapsulated (encapsulation material not shown) may be a thin layer 643, and between the haptics and this layer (made of for example, acrylic material) may be an aformentioned energy harvester as in FIG. 6d-g, formed of an electrode layer, positively charged nanofiber layer, negatively charged nanofiber layer, and finally another electrode layer. The nanofibers being encapsulated preferably hermetically, have substantially no contact with the electrolytes in the aqueous. Several projections 644 may be in contact with the ciliary sulcus, creating a minimal pressure on the surrounding tissue and enabling the adaptation of the energy harvesting mechanism to various diameters of ciliary sulcii (e.g. for different patients). The ciliary muscle pushes against the projections 644 and then relaxes in directions of double pointed arrow 652 (i.e. pushing in down and relaxing is up in arrow 652) leads to intermittent contact between the nanofibers, creating a charge as described above with respect to FIGS. 6d-g. The relaxation of the ciliary muscle which increases its diameter, allows the energy harvesting mechanism to return to its previous shape due to the elasticity of the encapsulant material.

Figure 8B:
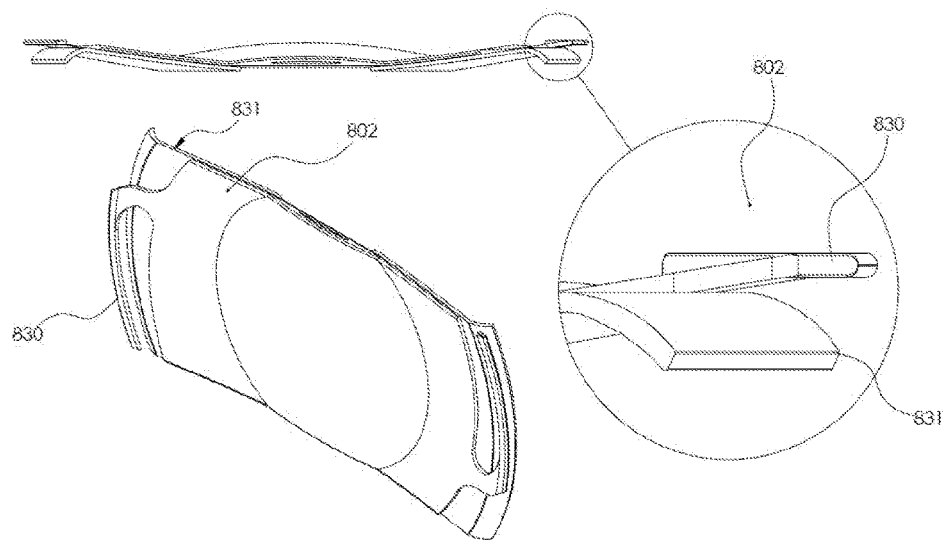
Figure 8B:
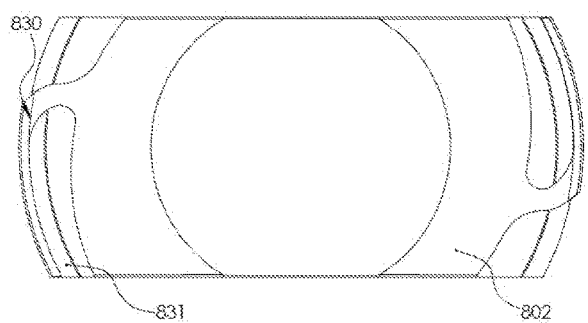

FIG. 8 shows a cross section of an optional embodiment of the lens optic and haptics, with the sliding encapsulated mover 800 and stator 802. The mover 800 possibly here ends in a protrusion, possibly bent protrusion (see enlarged section to the right of FIG. 8) so as to be in contact with the ciliary muscle, while the stator part 802 of the haptics is inside the ciliary sulcus. This embodiment enables support of the lens, while allowing for movement of the mechanism without causing decentration with respect to the line of sight. An angle 803 (Ang 1) and a length dimension 804 (D2) are typical dimensions of the ciliary sulcus, where Ang 1 is approximately 65° and D2 is approximately 0.5 mm.

FIG. 8a shows the position of an embodiment of FIG. 8 in the eye. The stator part of the haptic is in contact with the ciliary sulcus 820 while the mover part 822 is in contact preferably with an anterior part of the ciliary process 821. Other structures are the iris 823, zonules 825 and the outline of the capsular bag 824 when filled with the crystalline lens, which is no longer present after phacoemulsification, leaving the capsular bag 824 collapsed.

Both the ciliary sulcus and the ciliary process move radially inward (i.e. towards the optical axis) during accommodation, releasing tension in the zonular fibers. There may be benefit in having as large a relative motion as possible between the stator and mover which directly affects the energy harvested. The stator part of the haptics in an embodiment is designed to absorb the motion of the ciliary muscle, keeping the lens in the same position, while the mover transmits the force of the ciliary muscle to movement of the energy harvesting mechanism.

A possible method to absorb the movement may be by creating a resilient member 830 at an outer radial portion of the stator haptic 802, here possibly shown having a cantilever-like shape as in C-loop haptics, (see FIG. 8b). The mover part 831 of the haptic is here separated from the stator 802 close to the contact area with the ciliary muscle, so that resilient member 830 absorbs movement from the muscle fibers in the ciliary sulcus to substantially allow stator 802 to remain in place, while mover 831 exposed to movement of the ciliary muscle (preferably an anterior part of said muscle) is left to move to facilitate harvesting of energy.

Figure 8C:
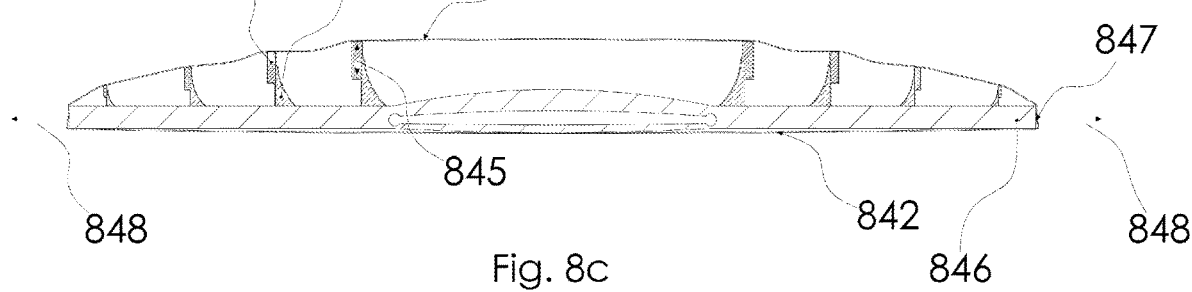

A similar embodiment can be realized for an intraocular lens being implanted in the capsular bag (see 824 in FIG. 8A), in which the energy harvesting mechanism may be positioned to take advantage of movement of the capsular bag tissue caused by the ciliary muscle, against the haptics. In FIG. 8c, this case is shown in which a stator part of the haptics 846 may possibly be positioned to be in contact with the equator 847 of the capsular bag and a mover 843 may be in contact with the anterior portion 840 of the capsular bag and the posterior portion 842 of the capsular bag (shown here only in contact with the anterior portion 840 of the capsule) and move in proximity to an additional stator 844, to absorb the stretching movement of the capsule in the axial direction (movement direction shown by arrow 845, capsule is stretched in the transverse direction shown by arrows 848). The capsulorrhexis is not shown in this drawing.

In essence, the functional mechanism of the energy harvesting components whether implanted in the ciliary sulcus or the capsular bag is substantially similar, in this example differing in the vectors of mechanical forces and the resulting geometry of the stator and mover to best utilize these forces.

Adjustable Haptics

In some embodiments the overall structure of the haptics may be adjustable in their total diameter so that they may be configured to exert substantially similar force when in contact with different ciliary sulcus or capsular bag sizes, for example by way of a sliding mechanism that is locked in a rigid manner once reaching the desired position.

Figures 9A, 9B:
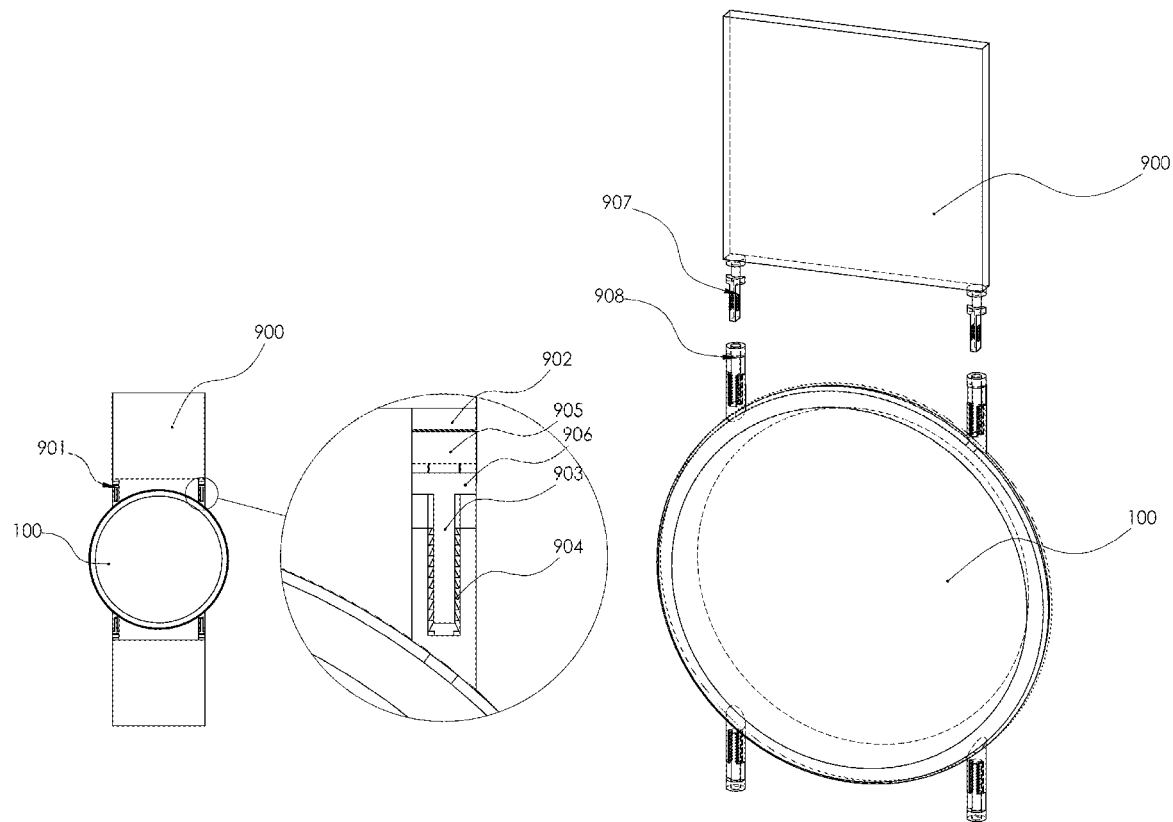
FIGS. 9a and 9b schematically show possible arrangement of intraocular lenses and/or haptic embodiments in relation to element of a human eye.

FIGS. 9a and 9b schematically illustrate an aspect of the present invention where an embodiment may be provided in which a haptics 900 (possibly a haptics including energy harvesting components but not necessarily) may be connected to an optic body 100 via adjustable coupling means 901. The coupling means 901 may include first members 907 on the haptics that are configured to couple with respective second members 908 on the optic body 100.

The first members in this example may take a form of struts with teeth like formations that are configured to be received in respective teeth formations on the second members to form a ratchet like meshing mechanism 904.

A surgeon may manipulate the position of the haptics relative to the optic body, by urging the first and second members to slide one in relation to the other in order to slightly bias the haptics away or towards the optic body. In the possible ratchet like meshing mechanism 904 this may be facilitated by slightly expanding a distance between the teeth on the struts of the optic body in order to enable the teeth of the haptic struts to progress to a subsequent position enabling either the haptics to bias closer or further away from the optic body.

Such adjustable coupling means 901 may be used to attach an optic body to haptics including energy harvesting means in order to enable fine adjustment of the position of the haptics relative e.g. to the ciliary muscle in order to optimize the force exerted by the muscle e.g. on a mover (such as mover 800) so that it may efficiently move against a stator (such as stator 802 seen in previous embodiments). Such fine adjustment, which on the one hand enables fine tuning of the haptics relative to the muscle, substantially does not change the overall position of the haptics (possible with energy harvesting mechanism) relative to the optic body for a given ciliary muscle diameter of a certain patient.

In an embodiment, the adjustable coupling means may include stoppers 902 and 903 on the first members 907 and corresponding stoppers 905 on the second members 908 of the optic body, in order to constrain the range of adjustment and by that avoid e.g. detachment of the haptics from the optic body.

Limiting the range of adjustment may facilitate adjustment of the overall diameter of the IOL within a given range, possibly between about 9.5 mm and about 13 mm, covering typical requirements for most patients of all ages. This embodiment may be advantageous in the case of IOL implantation in children or in ageing patients, where the natural growth of the eye may change the ciliary muscle diameter, or correction for weakening ciliary muscle may be performed, e.g. in secondary procedures later in life.

In one or more embodiments additional flexible struts may be incorporated into the optic-haptic junction to allow for wiring or other means of electrical communication between the energy harvesting mechanism and the optic body/actuating mechanism.

In addition said adjustable haptics may be implemented in conjunction with any IOL, not necessarily having an energy harvesting mechanism or an actuating lens, where simple surgical manipulation with standard tools such as Sinskey hooks, Kuglen hooks, choppers, spatulas, holders or forceps may adjust the overall diameter of a lens by increasing the separation distance between said haptics and optic body to fit the IOL in various ciliary sulcus and/or capsular bag sizes, pre-empting e.g. the need for pre-operational ultrasound biomicroscopy (UBM) measurements to determine said sizes, and reducing the need for various diameter sizes of an IOL.

Signal Processing, Energy Storage and Control

An embodiment of a motion sensor 700 is shown in a lumped diagram in FIG. 7.

In an embodiment energy harvested by the motion sensor 700 may be stored in an energy storage component 702 such as a miniaturized capacitor or a battery, or plurality of the same, embedded in the lens material outside of the clear optic, and serving as a power source.

In one embodiment of the invention, the operation of the actuating lens 705 is controlled by a microcontroller 703 embedded in the lens body material, in an area that is outside of the clear optic diameter.

An analogue to digital (A/D) converter 701 may be employed to quantize the input voltage from the motion sensor 700 possibly by receiving energy from energy storage 702 for its function. The quantized signal is in turn passed possibly to a digital signal processor (DSP, not shown) for passing the correct logic to the microcontroller 703. Possibly, microcontroller 703 may define said logic. Microcontroller 703 in addition may receive energy from storage 702 for its function. A threshold required to induce motion in an actuating lens and/or to maintain the actuated state may be defined according to a value of one or more of such quantization steps.

Regarding the number of steps in the quantization of the input signal, taking 4D as a nominal value of the maximal change in focus, and a maximal acceptable refractive error at the lens plane of 0.5D, the A/D converter may have 8 steps, or be a 3 bit converter as a minimal requirement. A 4 bit converter gives 0.25D steps, which may be preferred. At this resolution there is little significance from a patient perception to the quantization error.

Once an accommodative response is sensed by the motion sensor 700, the electric signal is directed to the microcontroller 703 which in turn causes the energy storage 702 to direct a current into the actuating lens circuit 705. This creates the deflection and curvature change required in the actuating lens. Signal generator 707 may generate an AC signal depending on the resonant frequency of a piezoelectric actuator or DC signal in the case of a dielectric elastomer actuator. In some cases, excess energy above a certain step not reaching a level of a subsequent higher step may be conserved in energy storage 702 and not expended to create the deflection and curvature change in the actuating lens.

A low pass filter may be incorporated in the microcontroller logic circuitry to provide a clear trigger signal for actuation, be it far-to-near or near-to-far accommodation depending on the sign of the input.

Motion of the actuated lens would also create an electrical signal, either by way of the inverse piezoelectric effect or by capacitance changes stemming from changes in the plate separation distance during actuation. Such a signal would result in a reverse current, also guided by the circuitry 706 to the energy storage components. A diode may be used for this purpose. Thus the energy used by the actuating lens may be conserved.

All circuitry may be part of the lens and embedded into the lens material.

It may be necessary to create varied curvature responses to differing accommodative demands both for piezoelectric or dielectric elastomer based lenses. In the case of a piezoelectric based lens, this may be achieved by supplying power in one or more AC frequencies possibly with differing amplitudes and/or DC offsets, provided by a signal generator possibly similar to signal generator 707. In the case of a dielectric based lens, a DC voltage in differing magnitudes across the electroactive material layer (EAM) may create such varied curvatures.

In an embodiment of a piezoelectric based lens, provision of the AC voltage may be with a non-zero (possibly negative or positive) DC offset correlating to the required or targeted lens curvature, with such DC offset urging the lens away from its resting state, possibly against the lens elasticity acting to urge the lens back to it resting state. Frequency may depend on variable factors such as stiffens of lens and geometry of the lens.

Different accommodative responses may be expressed in the variance in changes of the ciliary muscle ring diameter (CMRD), as well as other structures that are part of the ciliary process that the sensor may detect. Calibration and/or setting of the threshold for each discretized position of the ciliary muscle vs EAM layer deflection in an embodiment is suggested by way of prior measurement of the typical amplitude of motion of a given patient by using Anterior Segment Optical Coherence Tomography (AS-OCT). This may be performed immediately after removing the cataractous lens. In a non-binding example this "binning" of threshold levels may be decided in advance, for instance by using an average value between 0.02 mm and 0.105 mm in change of CMRD per diopter (D). Possibly, the setting of the threshold may be affected by considerations such as manufacturing and/or design considerations stemming e.g. from an EAM and/or substrate layer thickness, number of EAM and/or substrate layer (etc).

Near Infrared Energy Harvesting

In another aspect of the energy harvesting method, the energy may be harvested from a series of photovoltaic cells that absorb near infra-red light, of wavelengths between 750 nm and 900 nm. These wavelengths are not significantly absorbed by the skin, bone and eye tissue, especially not in the typical tissue depths from between the outside world and up to the IOL. This is a source of energy that is useful for harvesting during daylight hours, in which approximately 50% of light reaching the eye is in the IR range. Since visible light would only go through the pupil, the relative amount of energy of unabsorbed NIR light would be much higher.

While UV light is also prevalent, in the crystalline lens and in most IOL materials it is blocked or filtered, as UV is one of the causes of cataracts and is harmful to the retina. In addition to this the lifetime of UV-absorbing photovoltaic cells would be shorter than at working at other wavelengths, which is undesirable in a biomedical implant.

The photovoltaic cells may be anywhere on the lens body outside the clear optic, in a manner that does not interfere with the actuation of the lens or encumber the folding or injection of the lens. The photovoltaic cells would preferably be biocompatible, and in any case be embedded in the lens material, which is transparent to NIR wavelengths.

In an embodiment the light energy arriving through the pupil may be absorbed by a transparent dye or dye suspension, formed in between an anterior NIR-transparent layer and posterior NIR-reflective layer, and forms a waveguide. The anterior and posterior layers are both transparent to visible light. The NIR light is absorbed in this dye layer, and then via the Stokes shift the dye emits light at another NIR wavelength that is guided to the photovoltaic cells.

The lens may be packaged in a preloaded injector or delivery device which enables simple use and delivery into the eye, preferably through a small incision in the cornea or limbus as is known to those skilled in the art.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

Furthermore, while the present application or technology has been illustrated and described in detail in the drawings and foregoing description, such illustration and description are to be considered illustrative or exemplary and non-restrictive; the technology is thus not limited to the disclosed embodiments. Variations to the disclosed embodiments can be understood and effected by those skilled in the art and practicing the claimed technology, from a study of the drawings, the technology, and the appended claims.

In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage.

The present technology is also understood to encompass the exact terms, features, numerical values or ranges etc., if in here such terms, features, numerical values or ranges etc. are referred to in connection with terms such as "about, ca., substantially, generally, at least" etc. In other words, "about 3" shall also comprise "3" or "substantially perpendicular" shall also comprise "perpendicular". Any reference signs in the claims should not be considered as limiting the scope.

Although the present embodiments have been described to a certain degree of particularity, it should be understood that various alterations and modifications could be made without departing from the scope of the invention as hereinafter claimed.

The invention claimed is:

1. An intraocular lens (IOL) comprising a polymeric clear optic and an actuator for actuating change in curvature in at least a portion of the clear optic, the clear optic comprising a polymer substrate formed on opposite sides of the actuator, wherein the actuator comprises a pair of negative and positive transparent electrodes and an electroactive material (EAM) placed between and in direct contact with the electrodes, and wherein change in curvature is formed by applying voltage between the electrodes, wherein upon cessation of actuation in curvature change the clear optic is configured to elastically return towards a non-actuated resting state, wherein said resting state is at least one of a convex-concave state or concave-convex state, wherein the clear optic comprises (i) an anterior lens formed from a transparent optical material and providing baseline optical power for far vision, (ii) a posterior lens formed from a transparent optical material and providing optical power for near vision, (iii) an annular bridge formed about a periphery of the clear optic and connecting the anterior lens to the posterior lens, and (iv) an annular fluid reservoir, wherein the anterior and posterior lenses are spaced apart by a central cavity, wherein said central cavity is filled with silicone oil or a soft gel, wherein the annular bridge is formed with passages or fenestrations for providing fluid communication between the central cavity and the annular fluid reservoir, wherein the electroactive material comprises a piezoelectric polymer and/or a dielectric elastomer material, wherein the actuator comprising a stack of electroactive material layers (EAMs) with interdigitated electrodes, wherein adjacent electrodes being oppositely charged, wherein the actuator urges change in curvature in at least one of the anterior and posterior lenses.

2. The IOL of claim 1, wherein the electrodes are formed in contact with different areas of the clear optic.

3. The IOL of claim 1 wherein the electroactive material comprises a dielectric elastomer material which is a soft and passive dielectric material with a high Poisson ratio, sandwiched between compliant electrodes.

4. The IOL of claim 3 wherein the electrodes are transparent conductors covering the surfaces of the dielectric elastomer material.

5. The IOL of claim 3 wherein the electrodes are silver nanowires patterned over the surfaces of the dielectric elastomer material, without decreasing the transmission of light through the lens to below 90% in the visible range.

6. The IOL of claim 1, wherein cessation includes discharging a voltage present in the actuator.

7. The IOL of claim 1, wherein the actuator comprises an annular electrode formed along at least a portion of a periphery of one of a posterior or anterior side of the actuator and at least one other electrode formed on at least a portion of an opposing side of the actuator, wherein the annular electrode having a similar polarity to the other electrode to assist in the urging of curvature.

8. The IOL of claim 7, wherein the assisting in the urging of curvature is due to repulsion between the annular electrode and the at least one other opposing electrode.

9. The IOL of claim 8, wherein the repulsion increases thickness in a region of the actuator adjacent the annular electrode.

10. The IOL of claim 1, wherein the urging of change is in the posterior lens.

11. The IOL according to claim 1, wherein the piezoelectric polymer comprises fiber structures.

12. The IOL according to claim 11, wherein the fiber structures are formed by electrospinning.

13. The IOL according to claim 12, wherein the fiber structures are patterned as a continuous spiral.

14. The IOL according to claim 13, wherein a pitch of the spiral is such that there is a gap between arms of the spiral substantially eliminating electrical contact between said arms.

15. The IOL according to claim 11, wherein a poling direction of the fiber structures is parallel to a length dimension of the fiber structures.

16. The IOL according to claim 15, wherein the fiber structures are configured as hollow tubes.

17. The IOL according to claim 15, wherein the fiber structures are coaxially electrospun with a transparent conductor as the core material.

18. The IOL according to claim 11, wherein the fiber structures are coaxially electrospun with a transparent conductor both as a core and as an outer layer around the piezoelectric polymer.

19. The IOL according to claim 1, wherein motion of the actuated lens creates an electrical signal, either by way of an inverse piezoelectric effect or by capacitance changes stemming from changes in distance between electrodes during actuation, wherein said signal and/or energy being stored in a storage unit of the IOL.

20. The IOL of claim 1, wherein the materials of the dielectric elastomer of the lens element are spin-coated, electrosprayed and spin coated, injection molded, cast molded, cast and pressed, pad printed, 3D printed or cryogenically lathed from stock material.

* * * * *